(12) United States Patent
Huang et al.

(10) Patent No.: US 11,571,480 B2
(45) Date of Patent: Feb. 7, 2023

(54) MULTI-LIGAND DRUG CONJUGATES AND USES THEREOF

(71) Applicant: COHERENT BIOPHARMA I, LIMITED, Hong Kong (HK)

(72) Inventors: Baohua Robert Huang, Suzhou (CN); Jian Dai, Suzhou (CN); Zhongbo Wang, Suzhou (CN); Xueyuan Xie, Suzhou (CN); Xiaodong Liu, Suzhou (CN); Xinli Hu, Suzhou (CN)

(73) Assignee: Coherent Biopharma I, Limited, Hong Kong (HK)

( * ) Notice: Subject to any disclaimer, the term of this patent is extended or adjusted under 35 U.S.C. 154(b) by 0 days.

(21) Appl. No.: 15/751,541

(22) PCT Filed: Aug. 11, 2016

(86) PCT No.: PCT/CN2016/094704
§ 371 (c)(1),
(2) Date: Feb. 9, 2018

(87) PCT Pub. No.: WO2017/025057
PCT Pub. Date: Feb. 16, 2017

(65) Prior Publication Data
US 2018/0200377 A1    Jul. 19, 2018

(30) Foreign Application Priority Data

Aug. 11, 2015 (CN) .......................... 201510489556.6
Aug. 11, 2015 (CN) .......................... 201510489560.2

(51) Int. Cl.
| | | |
|---|---|---|
| A61K 47/64 | (2017.01) | |
| A61K 47/65 | (2017.01) | |
| A61K 47/55 | (2017.01) | |
| A61K 45/06 | (2006.01) | |
| C07K 14/705 | (2006.01) | |
| A61K 31/519 | (2006.01) | |
| A61P 37/02 | (2006.01) | |
| A61P 35/00 | (2006.01) | |
| A61K 31/401 | (2006.01) | |

(52) U.S. Cl.
CPC ............ *A61K 47/64* (2017.08); *A61K 31/519* (2013.01); *A61K 45/06* (2013.01); *A61K 47/551* (2017.08); *A61K 47/65* (2017.08); *A61P 35/00* (2018.01); *A61P 37/02* (2018.01); *A61K 31/401* (2013.01); *C07K 14/705* (2013.01)

(58) Field of Classification Search
CPC ..... A61K 47/64; A61K 47/551; C07K 14/705
See application file for complete search history.

(56) References Cited

U.S. PATENT DOCUMENTS

| | | | |
|---|---|---|---|
| 10,172,953 B2 | 1/2019 | Schellenberger et al. | |
| 2005/0171014 A1* | 8/2005 | Tarasova | C07K 14/595 514/11.1 |
| 2005/0181992 A1 | 8/2005 | Stewart et al. | |
| 2007/0259008 A1 | 11/2007 | Ljubimova et al. | |
| 2008/0279868 A1 | 11/2008 | Medarex | |
| 2011/0059076 A1* | 3/2011 | McDonagh | C07K 16/32 424/133.1 |
| 2011/0230420 A1 | 9/2011 | Zhao et al. | |
| 2014/0030282 A1 | 1/2014 | Polakis et al. | |
| 2015/0105540 A1 | 4/2015 | Miao et al. | |
| 2017/0202970 A1* | 7/2017 | Foreman | C08G 77/452 |

FOREIGN PATENT DOCUMENTS

| | | | | |
|---|---|---|---|---|
| CA | 2837979 A2 | 12/2012 | | |
| CN | 101224306 A | 7/2008 | | |
| CN | 103372199 A | * 10/2013 | | |
| CN | 104667292 A | 6/2015 | | |
| TL | 2014001798 A1 | 1/2014 | | |
| WO | 9959640 A2 | 11/1999 | | |
| WO | 03034995 A2 | 5/2003 | | |
| WO | 03092737 A1 | 11/2003 | | |
| WO | 2006060664 A2 | 6/2006 | | |
| WO | 2007022494 A2 | 2/2007 | | |
| WO | 2008034124 A2 | 3/2008 | | |
| WO | 2008094834 | 8/2008 | | |
| WO | 2010057154 A1 | 5/2010 | | |
| WO | 2012019121 A2 | 2/2012 | | |
| WO | 2013170272 A2 | 11/2013 | | |
| WO | 2014009774 A1 | 1/2014 | | |
| WO | 2014086835 A1 | 6/2014 | | |
| WO | 2014089209 A2 | 6/2014 | | |
| WO | 2014144600 A2 | 9/2014 | | |
| WO | 2015106599 A1 | 7/2015 | | |
| WO | WO-2015106599 A1 * | 7/2015 | ............ | A61K 47/65 |

(Continued)

OTHER PUBLICATIONS

Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Lazar et al. Transforming Growth Factor alpha: Mutation of Aspartic Acid 47 and Leucine 48 Results in Different Biological Activities . Mol. Cell. Biol., 8:1247-1252, 1988 (Year: 1988).*
Bork. Powers and Pitfalls in Sequence Analysis: The 70% Hurdle. Genome Research, 2000; 10:398-400 (Year: 2000).*

(Continued)

*Primary Examiner* — Vanessa L. Ford
*Assistant Examiner* — Sandra Dillahunt

(57) ABSTRACT

A conjugate compounds or pharmaceutically acceptable salt thereof, comprises a payload and two or more kinds of cell-interacting molecules. The cell-interacting molecules are ligands capable of specifically binding to a cell surface receptor. A method of treating diseases, comprises delivering a payload to a subject.

6 Claims, 9 Drawing Sheets

Specification includes a Sequence Listing.

(56) References Cited

FOREIGN PATENT DOCUMENTS

WO     WO-2016004043 A1 *   1/2016            A61K 47/542

OTHER PUBLICATIONS

Zong et al. Synergistic Dual-Ligand Doxorubicin Liposomes Improve Targeting and Therapeutic Efficacy of Brain Glioma in Animals. Molecular Pharmaceutics, 2014, 11:2346-2357 (Year: 2014).*
Bowie et al. Science, 1990, 247:1306-1310 (Year: 1990).*
Burgess et al. J. Cell Biol. 111:2129-2138, 1990 (Year: 1990).*
Lazar et al. (Mol. Cell. Biol., 8:1247-1252, 1988) (Year: 1988).*
Gavrilyuk et al. Bioorg. Med. Chem. Lett. 19 (2009) 3716-3720 (Year: 2009).*
Reddy et al. Folate Receptor-Specific Antitumor Activity of EC131, a Folate-Maytansinoid Conjugate. Cancer Res 2007;67(13): 6376-82 (Year: 2007).*
Reddy et al. Cancer Res 2007;67(13):6376-82 (Year: 2007).*
The International Search Report and Written Opinion, dated Nov. 25, 2016, in the related PCT patent application No. PCT/CN2016/094704.
The English translation of the Russian Office Action, dated Nov. 20, 2018, in the related Russian Patent Appl. No. 2018104266/20(006359).
Ahmad A., et al., "Daunorubicin coupled to monoclonal antibodies via a cis aconitic anhydride linker: biochemical and cytotoxic properties revisited," Anticancer Res. May-Jun. 1990;10(3):837-43, abstract.
Badr M., et al., "Methotrexate-gelonin conjugate—an inhibitor of MCF-7 cells expressing the dihydrofolate receptor," Biol Chem. Dec. 2014;395(12):1461-6. doi: 10.1515/hsz-2013-0270., abstract.
Dosio F., et al., "Immunotoxins and anticancer drug conjugate assemblies: the role of the linkage between components," Toxins (Basel). Jul. 2011. 14;3(7):848-83, abstract.
The Australian Examination Report, dated Jan. 24, 2019, in the related Australian Patent Appl. No 2016305703.
The Canadian Office Action, dated Dec. 14, 2018, in the related Canadian Patent Appl. No. 2,987,322.
Cleal, K. et al., "Endocytosis, Intracellular Traffic and Fate of Cell Penetrating Peptide Based Conjugates and Nanoparticles", Current Pharmaceutical Design, (2013) vol. 19, No. 16, pp. 2878-2894.
Safavy et al., "Single-drug multiligand conjugates: Synthesis and preliminary cytotoxicity evaluation of a paclitaxeldipeptide "Scorpion" molecule", Bioconjugate Chemistry, 2006, 17(3), 565-570.
Kakimoto et al., "Dual-ligand effect of transferrin and transforming growth factor alpha on polyethyleneimine-mediated gene delivery", Journal of Controlled Release, 2007, 120(3), 242-249.
Torchhilin, "Multifunctional nanocarriers", Advanced Drug Delivery Reviews, 2006, 58(14), 1532-1555.
Majoros et al., "PAMAM dendrimer-based multifunctional conjugate for cancer therapy: Synthesis, characterization and functionality", Biomacromolecules, 2006, 7(2), 572-579.
Paleos et al., "Drug delivery using multifunctional dendrimers and hyperbranched polymers", Expert Opinions on Drug Delivery, 2010, 7(12), 1387-1398.

The English translation of the Japanese Office Action, dated Mar. 19, 2019, in the related Japanese Appl. No. 2017-568345.
Canal et al., "Relevance of folic acid/polymer ratio in targeted PEG—epirubicin conjugates," Journal of Controlled Release 146 (2010) 388-399.
The extended European search report, dated Mar. 1, 2019, in the related European Patent Appl. No. 16834681.5.
Young Choi et al: "Folic acid-tethered Pep-1 peptide-conjugated liposomal nanocarrier for enhanced intracellular drug delivery to cancer cells: conformational characterization and in vitro cellular uptake evaluation", International Journal of Nanomedicine, Mar. 15, 2013 (Mar. 15, 2013), p. 1155, XP55554721.
Jianian Chen et al: "Folic acid and cell-penetrating peptide conjugated PLGA-PEG bifunctional nanoparticles for vincristine sulfate delivery", European Journal of Pharmaceutical Sciences., vol. 47, No. 2, Sep. 1, 2012 (Sep. 1, 2012), pp. 430-143, XP055554726.
Gao Wei et al: "Chemotherapeutic drug delivery to cancer cells using a combination of folate targeting and tumor microenvironment-sensitive polypeptides", Biomaterials, Elsevier Science Publishers BV., Barking, GB, vol. 34, No. 16, Mar. 1, 2013 (Mar. 1, 2013), pp. 4137-1149, XP028997308.
Kazuhiro Takara et al: "Size-controlled, dual-ligand modified liposomes that target the tumor vasculature show promise for use in drug-resistant cancer therapy", Journal of Controlled Release, vol. 162, No. 1, Aug. 1, 2012 (Aug. 1, 2012), pp. 225-232, XP055554551.
Saul J M et al: "A dual-ligand approach for enhancing targeting selectivity of therapeutic nanocarriers", Journal of Controlled Release, Elsevier, Amsterdam, NL, vol. 114, No. 3, Sep. 12, 2006 (Sep. 12, 2006), pp. 277-287, XP024957616.
Nukolova et al., "LHRH-targeted nanogels as a delivery system for cisplatin to ovarian cancer," Mol Pharm. Oct. 7, 2013;10(10):3913-21.
Lehen'kyi et al., "TRPV6 channel controls prostate cancer cell proliferation via Ca2 þ / NFAT—dependent pathways," Oncogene (2007) 26, 7380-7385.
Virgolini et al., "Somatostatin Receptor Subtype Specificity and in Vivo Binding of a Novel Tumor Tracer, 99mTc-P829," Cancer Res. May 1, 1998;58(9):1850-9.
Versteeg et al., "Protease-Activated Receptor (PAR) 2, but not PAR1, Signaling Promotes the Development of MammaryAdenocarcinoma in Polyoma Middle T Mice," Cancer Res. Sep. 1, 2008;68(17):7219-27.
The English translation of the Russian Office Action, dated Sep. 11, 2019, in the related Russian Patent Appl. No. 2018104266.
The English translation of the Japanese Office Action, dated Oct. 1, 2019, in the related Japanese Patent Appl. No. 2017-568345.
Hagner, Nicole, and Markus Joerger. "Cancer chemotherapy: targeting folic acid synthesis." Cancer management and research vol. 2 293-301. Nov. 19, 2010.
The English translation of the Japanese Office Action, dated Feb. 18, 2020, in the related Japanese Appl. No. 2017-568345.
Chen et al., "Application of Luteinizing Hormone—Releasing Hormone for Cancer Therapy," Strait Pharmaceutical Journal, 2014, vol. 26 (9), p. 80-84. (The English abstract included).
Brazeau et al., "Hypothalamic polypeptide that inhibits the secretion of immunoreactive pituitary growth hormone," Science, Jan. 5, 1973; 179(4068), p. 77-79.

* cited by examiner

LDC10B

LDC11B

LDC12B

LDC13B

LDC10H

LDC11H

LDC12H

LDC10BR

LDC10BX

LDC1013

Folate-FITC

10A-FITC

10B-FITC

SEQUENCE LISTING

```
<160> NUMBER OF SEQ ID NOS: 20

<210> SEQ ID NO 1
<211> LENGTH: 7
<212> TYPE: PRT
<213> ORGANISM: Artificial Sequence
<220> FEATURE:
<223> OTHER INFORMATION: Recognition Site for Matripase

<400> SEQUENCE: 1

Lys Ser Arg Ala Glu Asp Glu
1               5

<210> SEQ ID NO 2
<211> LENGTH: 6
<212> TYPE: PRT
<213> ORGANISM: Artificial Sequence
<220> FEATURE:
```

```
<223> OTHER INFORMATION: Recognition Site for MMP-2

<400> SEQUENCE: 2

Pro Leu Gly Leu Ala Gly
1               5

<210> SEQ ID NO 3
<211> LENGTH: 4
<212> TYPE: PRT
<213> ORGANISM: Artificial Sequence
<220> FEATURE:
<223> OTHER INFORMATION: Recognition Site for Prostate Specific Antigen

<400> SEQUENCE: 3

Ser Ser Leu Tyr
1

<210> SEQ ID NO 4
<211> LENGTH: 7
<212> TYPE: PRT
<213> ORGANISM: Artificial Sequence
<220> FEATURE:
<223> OTHER INFORMATION: Recognition Site for TMPRSS2

<400> SEQUENCE: 4

Leu Leu Arg Ser Leu Ile Gly
1               5

<210> SEQ ID NO 5
<211> LENGTH: 4
<212> TYPE: PRT
<213> ORGANISM: Artificial Sequence
<220> FEATURE:
<223> OTHER INFORMATION: Recognition Site for Activated Protein C

<400> SEQUENCE: 5

Leu Val Lys Arg
1

<210> SEQ ID NO 6
<211> LENGTH: 4
<212> TYPE: PRT
<213> ORGANISM: Artificial Sequence
<220> FEATURE:
<223> OTHER INFORMATION: Recognition Site for Factor Ixa

<400> SEQUENCE: 6

Leu Val Val Arg
1

<210> SEQ ID NO 7
<211> LENGTH: 4
<212> TYPE: PRT
<213> ORGANISM: Artificial Sequence
<220> FEATURE:
<223> OTHER INFORMATION: Recognition Site for Factor VIIa

<400> SEQUENCE: 7

Gln Leu Thr Arg
1

<210> SEQ ID NO 8
<211> LENGTH: 4
<212> TYPE: PRT
<213> ORGANISM: Artificial Sequence
<220> FEATURE:
<223> OTHER INFORMATION: Recognition Site for Factor Xa
```

```
<400> SEQUENCE: 8

Leu Glu Gly Arg
1

<210> SEQ ID NO 9
<211> LENGTH: 6
<212> TYPE: PRT
<213> ORGANISM: Artificial Sequence
<220> FEATURE:
<223> OTHER INFORMATION: Recognition Site for Calpain-a

<400> SEQUENCE: 9

Pro Leu Phe Ala Glu Pro
1               5

<210> SEQ ID NO 10
<211> LENGTH: 6
<212> TYPE: PRT
<213> ORGANISM: Artificial Sequence
<220> FEATURE:
<223> OTHER INFORMATION: Recognition Site for Calpain-2

<400> SEQUENCE: 10

Gly Leu Gly Ser Glu Pro
1               5

<210> SEQ ID NO 11
<211> LENGTH: 5
<212> TYPE: PRT
<213> ORGANISM: Artificial Sequence
<220> FEATURE:
<223> OTHER INFORMATION: Recognition Site for Enteropeptidase

<400> SEQUENCE: 11

Asp Asp Asp Asp Lys
1               5

<210> SEQ ID NO 12
<211> LENGTH: 4
<212> TYPE: PRT
<213> ORGANISM: Artificial Sequence
<220> FEATURE:
<223> OTHER INFORMATION: Recognition Site for MMP-8

<400> SEQUENCE: 12

Gly Pro Ser Gly
1

<210> SEQ ID NO 13
<211> LENGTH: 4
<212> TYPE: PRT
<213> ORGANISM: Artificial Sequence
<220> FEATURE:
<223> OTHER INFORMATION: Recognition Site for Prpprotein Covertase 5

<400> SEQUENCE: 13
```

```
Arg Ser Lys Arg
1

<210> SEQ ID NO 14
<211> LENGTH: 4
<212> TYPE: PRT
<213> ORGANISM: Artificial Sequence
<220> FEATURE:
<223> OTHER INFORMATION: Recognition Site for Calpain-3

<400> SEQUENCE: 14

Val Gly Val Phe
1

<210> SEQ ID NO 15
<211> LENGTH: 14
<212> TYPE: PRT
<213> ORGANISM: Artificial Sequence
<220> FEATURE:
<223> OTHER INFORMATION: P10

<400> SEQUENCE: 15

Cys Lys Glu Phe Leu His Pro Ser Lys Val Asp Leu Pro Arg
1               5                   10

<210> SEQ ID NO 16
<211> LENGTH: 11
<212> TYPE: PRT
<213> ORGANISM: Artificial Sequence
<220> FEATURE:
<223> OTHER INFORMATION: P11

<400> SEQUENCE: 16

Glu His Trp Ser Tyr Gly Leu Arg Pro Gly Cys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: P12

<400> SEQUENCE: 17

Ala Gly Cys Lys Asn Phe Phe Trp Lys Thr Phe Thr Ser Cys
1               5                   10

<210> SEQ ID NO 18
<211> LENGTH: 11
<212> TYPE: PRT
<213> ORGANISM: Artificial Sequence
<220> FEATURE:
<223> OTHER INFORMATION: P13
<220> FEATURE:
<221> NAME/KEY: MISC_FEATURE
<222> LOCATION: (6)..(6)
<223> OTHER INFORMATION: Xaa=D-Lys

<400> SEQUENCE: 18

Glu His Trp Ser Tyr Xaa Leu Arg Pro Gly Cys
1               5                   10
```

```
<210> SEQ ID NO 19
<211> LENGTH: 9
<212> TYPE: PRT
<213> ORGANISM: Artificial Sequence
<220> FEATURE:
<223> OTHER INFORMATION: R9

<400> SEQUENCE: 19

Arg Arg Arg Arg Arg Arg Arg Arg Arg
1               5

<210> SEQ ID NO 20
<211> LENGTH: 13
<212> TYPE: PRT
<213> ORGANISM: Artificial Sequence
<220> FEATURE:
<223> OTHER INFORMATION: Tat peptide

<400> SEQUENCE: 20

Gly Arg Lys Lys Arg Arg Gln Arg Arg Arg Pro Pro Gln
1               5                   10
```

MULTI-LIGAND DRUG CONJUGATES AND USES THEREOF

CROSS-REFERENCE TO RELATED APPLICATIONS

The present application is a National Stage Application of PCT/CN2016/094704 filed Aug. 11, 2016, which claims the benefit of priorities of Chinese Patent Application No. 201510489556.6, filed on Aug. 11, 2015, entitled "Ligand-Drug Conjugates Capable of Inducing Endocytosis," and Chinese Patent Application No. 201510489560.2, filed on Aug. 11, 2015, entitled "Multi-Ligand Drug Conjugates Capable of Inducing Endocytosis," each of prior mentioned applications is incorporated herein by reference in its entirety.

TECHNICAL FIELD

The present application relates generally to conjugate compounds, pharmaceutical compositions and methods of using the same. The present application is more specifically related to multi-ligand drug conjugates (mLDCs), especially mLDCs capable of inducing endocytosis, as well as their pharmaceutical compositions, methods of using the same in delivering payloads to subjects in need thereof, and methods of using the same in treating diseases.

BACKGROUND

Usually, the pathological and physiological characteristics of diseased cells and normal cells are significantly different, and one of the differences is that the surfaces of diseased cells have specific or overexpressed materials (such as, antigen, chemical signals, receptors, etc.), which are absent or lowly-expressed in normal cells. Based on this principle, antibody-drug conjugates (ADCs) and polypeptide-drug conjugates (PDCs) were developed for the treatment of diseases. Currently, although some ADCs and PDCs drugs were marketed or under clinical researches, there are many limitations on ADCs and PDCs in clinical due to the design rationale of these drugs.

ADCs have gained much foothold recently with the approval of Adcetris from Seattle Genetics in 2011 and Kadcyla from Genentech in 2013 and remains a hot R&D development area with over 30 drugs in clinical trials. Nonetheless, ADCs development faces a multitude of difficulties ranging from the lack of suitable targets, manufacturing hurdle and low drug stability due to the complex nature and large molecular weight of the ADCs. Currently, ADCs are mainly used in the treatment of cancers. In some instances, the affinity of the target antibody towards the antigen on cancer cell surface could be as high as $10^{-9} \sim 10^{-12}$ (Kd, mole/liter). Therefore, the ADCs, while having high specificity to target cells, also have high specificity to normal cells with the same target receptor(s) as the target cells. Meanwhile, it could take a long time (one to three weeks) to metabolize ADCs in vivo, during which it could continuously kill the normal cells, and thus significantly increase the toxic side effects of ADCs. Therefore, the more ideal indications of ADCs should be the diseases characterized in that the amounts of cell surface antigens in tumor and normal cells are significantly different. However, very few diseases known in the art can meet such strict requirement.

Another group of drug conjugate compounds are the ligand-drug conjugates (LDCs) where ligands are either peptide or small molecule. However, there are various problems to the application of LDCs, ranging from bioavailability, stability, efficacy, to toxicity. For example, many ligands are unable to enter into cells due to their large molecular weights, lipophilicity, or other attributes, limiting their therapeutic applications. In addition, the therapeutic effects are generally low if the ligands are conjugated with conventional chemotherapeutics (such as doxorubicin, paclitaxel, etc.), while the toxicities are high if they are conjugated with highly effective drug molecules (such as MMAE, DM1), and thus resulting in animal poisoning death even before the therapeutically effective amount is achieved for tumor treatment.

SUMMARY OF THE INVENTION

The present application relates to conjugate compounds or pharmaceutically acceptable salts thereof, their pharmaceutical compositions and methods of using the same. The present application is more specifically related to multi-ligand drug conjugates (mLDCs), especially mLDCs capable of inducing endocytosis, as well as their pharmaceutical compositions, methods of using the same in delivering payloads to subjects in need thereof, and methods of using the same in treating diseases, including but are not limited to, cancers, immunological diseases, cardiovascular diseases, metabolic diseases, and neurological diseases.

One aspect of the present application discloses a conjugate compound or a pharmaceutically acceptable salt thereof, comprising a payload and two or more kinds of cell-interacting molecules, wherein the payload is conjugated with at least one of the cell-interacting molecules.

In some embodiments, the payload is conjugated with at least one of the cell-interacting molecules directly. In some embodiments, the payload is conjugated with at least one of the cell-interacting molecules indirectly. In some embodiments, the payload is conjugated with at least one of the cell-interacting molecules via a linker. In some embodiments, at least one of the cell-interacting molecules is a ligand capable of binding to a cell surface receptor. In some embodiments, at least two of the cell-interacting molecules are ligands capable of binding to cell surface receptors.

In some embodiments, the conjugate compound or a pharmaceutically acceptable salt thereof comprises a first ligand capable of specifically binding to a first cell surface receptor, and a second ligand capable of specifically binding to a second cell surface receptor. In some embodiments, the conjugate compound or a pharmaceutically acceptable salt thereof comprises a first ligand capable of specifically binding to a first cell surface receptor, and a second ligand capable of specifically binding to a second cell surface receptor, wherein the first cell surface receptor and the second cell surface receptor are different from each other.

In some embodiments, the payload is conjugated with the first ligand, and the first ligand is conjugated with the second ligand. In some embodiments, the first ligand is conjugated with the second ligand directly. In some embodiments, the first ligand is conjugated with the second ligand indirectly. In some embodiments, the first ligand is conjugated with the second ligand via a spacer.

In some embodiments, the payload is conjugated directly with each of the first ligand and the second ligand without any linker. In some embodiments, the payload is conjugated with the first ligand via a first linker, and the payload is conjugated with the second ligand via a second linker. In some embodiments, the first linker and the second linker are the same. In some other embodiments, the first linker and the second linker are different. In some embodiments, the payload is conjugated with the first ligand directly without any linker, and the payload is conjugated with the second ligand via a linker.

In some embodiments, the conjugate compound or a pharmaceutically acceptable salt thereof further comprises a third ligand capable of specifically binding to a third cell surface receptor. In some embodiments, the first cell surface receptor, the second cell surface receptor and the third cell surface receptor are different from one another. In some embodiments, at least two of the first cell surface receptor, the second cell surface receptor, and the third cell surface receptor are different from one another. In some embodiments, the first ligand, the second ligand, and the third ligand are the same.

In some embodiments, the first, second and third cell surface receptor provided herein is independently selected from the group consisting of a transferrin receptor (TFR), a low-density lipoprotein receptor (LDLR), a folate receptor (FR), a uric acid kinase receptor, a tumor necrosis factor receptor (TNFR), integrin receptor LFA-1, somatostatin SST-14 receptor, luteinizing hormone releasing hormone (LHRH) receptor, TRPV6 receptor, and a protease surface antigen receptor.

In some embodiments, the first ligand, the second ligand and the third ligand are independently selected from the group consisting of a peptide, folate and analogs thereof.

In some embodiments, the ligand comprises a peptide having the amino acid sequence selected from the group consisting of Cys-Lys-Glu-Phe-Leu-His-Pro-Ser-Lys-Val-Asp-Leu-Pro-Arg (SEQ ID NO: 15, named as P10), Glu-His-Trp-Ser-Tyr-Gly-Leu-Arg-Pro-Gly-Cys (SEQ ID NO: 16, named as P11), Ala-Gly-[Cys-Lys-Asn-Phe-Phe-Trp-Lys-Thr-Phe-Thr-Ser-Cys], (SEQ ID NO: 17, named as P12), Glu-His-Trp-Ser-Tyr-D-Lys-Leu-Arg-Pro-Gly-Cys (SEQ ID NO: 18, named as P13), Arg-Gly-Asp (named as RGD), a homologous peptide having at least 70%, at least 80%, at least 85%, at least 90%, at least 91%, at least 92%, at least 93%, at least 94%, at least 95%, at least 96%, at least 97%, at least 98%, at least 99% amino acid sequence homology to any of SEQ ID NOs: 15-18, wherein the homologous peptides are functional equivalents of the peptides of SEQ ID NOs: 15-18, respectively.

In some embodiments, at least one of the cell-interacting molecules as described herein is an endocytosis molecule that is capable of mediating endocytosis. In some embodiments, the endocytosis molecule is also capable of specifically binding to a cell surface receptor.

In some embodiments, the endocytosis molecule is selected from the group consisting of folate and analogs thereof, a peptide capable of mediating endocytosis, and a cell-penetrating peptide.

In some embodiments, the linker provided herein is a peptide linker, a disulfide linker, or a pH-dependent linker.

In some embodiments, the peptide linker is cleavable under certain physiological environment by protease cleavage or reduction. In some embodiments, the peptide linker is selected from the group consisting of valine-citruline, phenylalanine-lysine, and valine-lysine.

In some embodiments, the disulfide linker is selected from the group consisting of DMDS, MDS, DSDM, and NDMDS.

In some embodiments, the pH-dependent linker is cis-aconitic anhydride.

In some embodiments, the conjugate compound or a pharmaceutically acceptable salt thereof comprises at least one payload. In some embodiments, the conjugate compound or a pharmaceutically acceptable salt thereof comprises one, two, three, four or more payloads.

In some embodiments, the payload is selected from the group consisting of a small molecule compound, a nucleotide, a peptide, a protein, and a nanoparticle. In some embodiments, the payload is a small molecule compound. In some embodiments, the payload is a therapeutic agent.

In some embodiments, the conjugate compound is a multi-ligand conjugate compound, which comprises a payload, two, three or more kinds of ligands, and optionally a linker or a spacer. In some embodiments, the conjugate compound is a bi-ligand conjugate compound, which comprises a payload, two kinds of ligands, and optionally a linker and/or a spacer. In some embodiments, the conjugate compound is a tri-ligand conjugate compound, which comprises a payload, three kinds of ligands, and optionally a linker and/or a spacer. In some embodiments, the conjugate compound is selected from the group consisting of the following compounds: LDC10B, LDC10BR, LDC10BX, LDC11B, LDC12B, LDC13B, LDC1013, LDC10H, LDC11H, LDC12H as shown in FIG. 1 herein.

Another aspect of the present application discloses a pharmaceutical composition comprising the conjugate compound provided herein, or a pharmaceutically acceptable salt thereof, and a pharmaceutically acceptable carrier. In some embodiments, the pharmaceutical composition is administered intravenously, subcutaneously, orally, intramuscularly, parenterally or intraventricularly.

Another aspect of the present application discloses a method for delivering a payload to a subject in need thereof, comprising administering to the subject a therapeutically effective amount of the conjugate compound provided herein, or a pharmaceutically acceptable salt thereof, or the pharmaceutical composition provided herein.

Another aspect of the present application discloses a method for treating a disease in a subject, comprising administering to the subject a therapeutically effective amount of the conjugate compound provided herein, or a pharmaceutically acceptable salt thereof, or the pharmaceutical composition provided herein. In some embodiments, the disease is selected from the group consisting of a cancer, an immunological disease, a cardiovascular disease, a metabolic disease, and a neurological disease.

In some embodiments, the cancer is selected from the group consisting of breast cancer, lung cancer, prostatic cancer, renal cancer, ovarian cancer, gastric cancer, uterine cancer, endometrial carcinoma, liver cancer, thyroid cancer, pancreatic cancer, colon cancer, colorectal cancer, esophageal cancer, skin cancer, lymphoma, leukemia, and multiple myeloma.

In some embodiments, the immunological disease is an autoimmune disease. In some embodiments, the autoimmune disease is selected from the group consisting of connective tissue disease, systemic sclerosis, rheumatoid arthritis, and systemic Lupus erythematosus.

In some embodiments, the cardiovascular disease is selected from the group consisting of angina, myocardial infarction, stroke, heart attack, hypertensive heart disease, rheumatic heart disease, cardiomyopathy, heart arrhythmia, and congenital heart disease.

In some embodiments, the metabolic disease is selected from the group consisting of diabetes, gout, obesity, hypoglycemia, hyperglycemia, and dyslipidemia.

In some embodiments, the neurological disease is selected from the group consisting of Alzheimer's disease, Parkinson's disease, Huntington's disease, head injury, multiple sclerosis, vertigo, coma, and epilepsy.

In some embodiments, the method provided herein further comprises administering one or more therapeutic agents in combination with the conjugate compound provided herein, or a pharmaceutically acceptable salt thereof, or the pharmaceutical composition provided herein. In some embodiments, the therapeutic agent targets an anti-cancer therapeutic target, induces or boosts immune response against cancer, or is a chemotherapeutic agent.

DETAILED DESCRIPTION OF THE INVENTION

Figure 1:
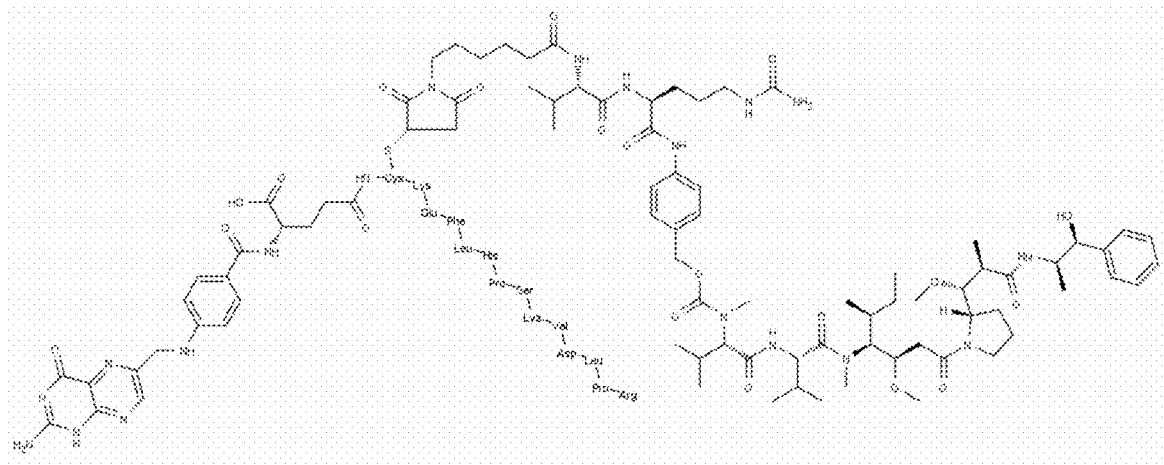
FIG. 1 shows the structures of LDC10B, LDC10BR, LDC10BX, LDC11B, LDC12B, LDC13B, LDC1013, LDC10H, LDC11H, and LDC12H.
Figure 1:
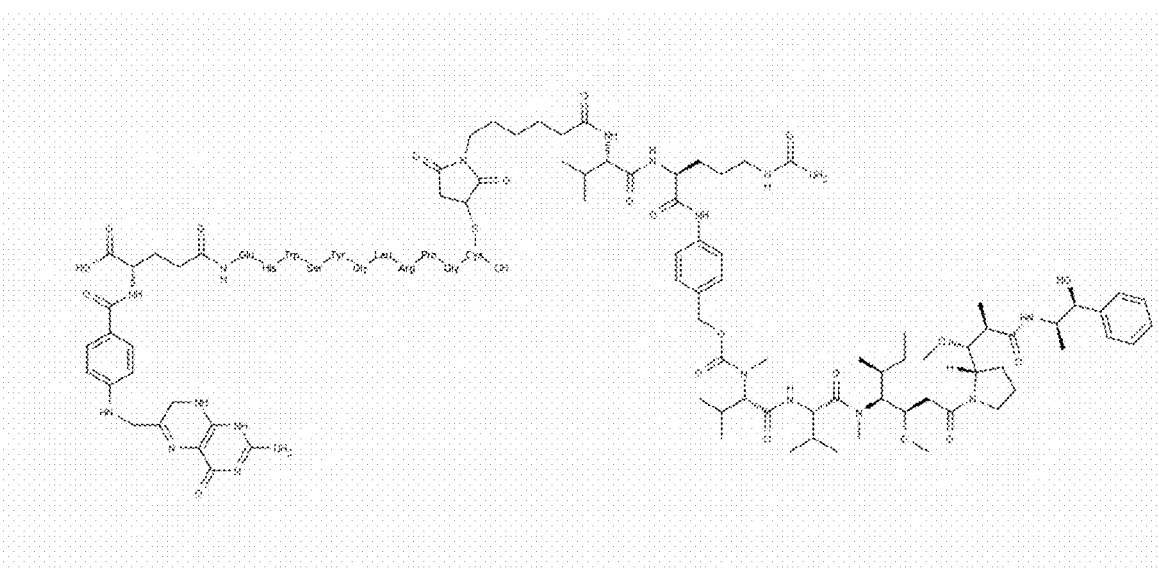
Figure 1:
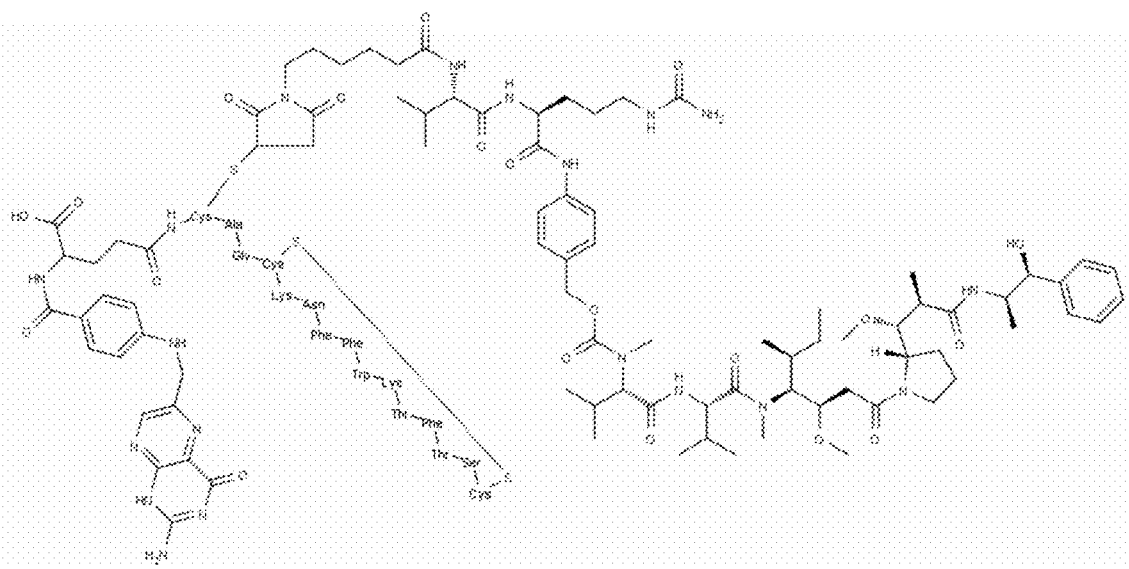
Figure 1:
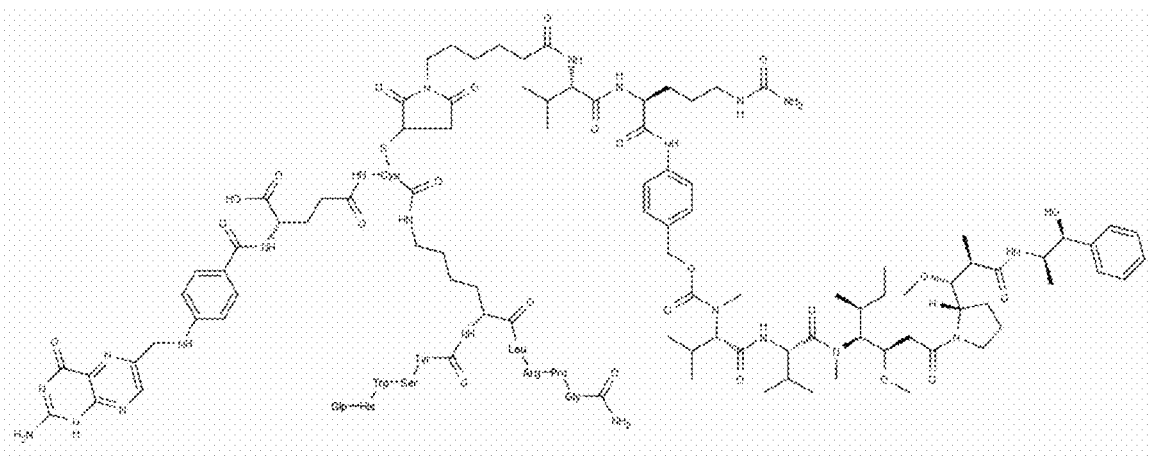
Figure 1:
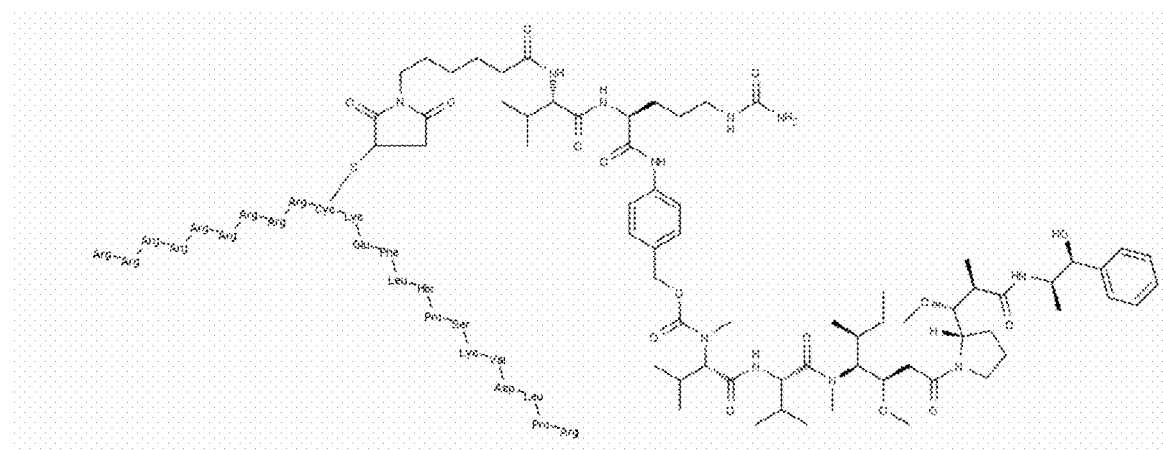
Figure 1:
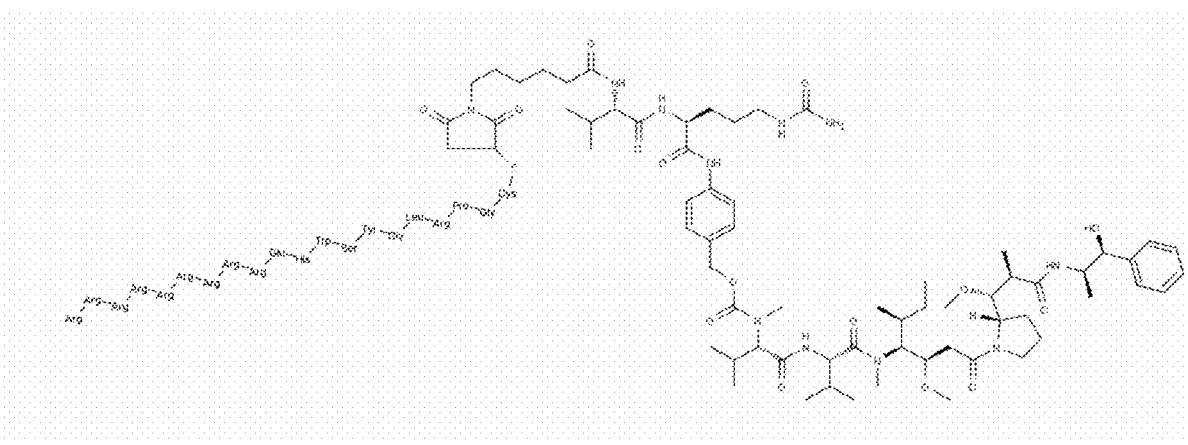
Figure 1:
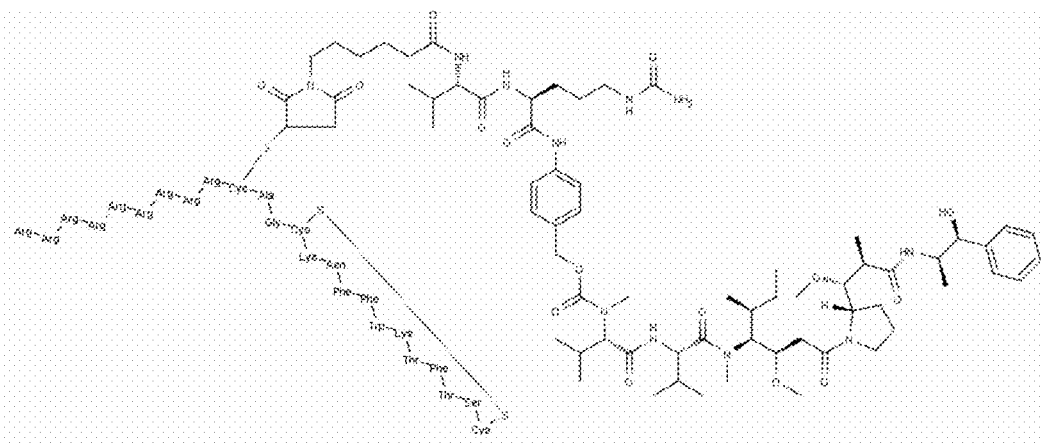
Figure 1:
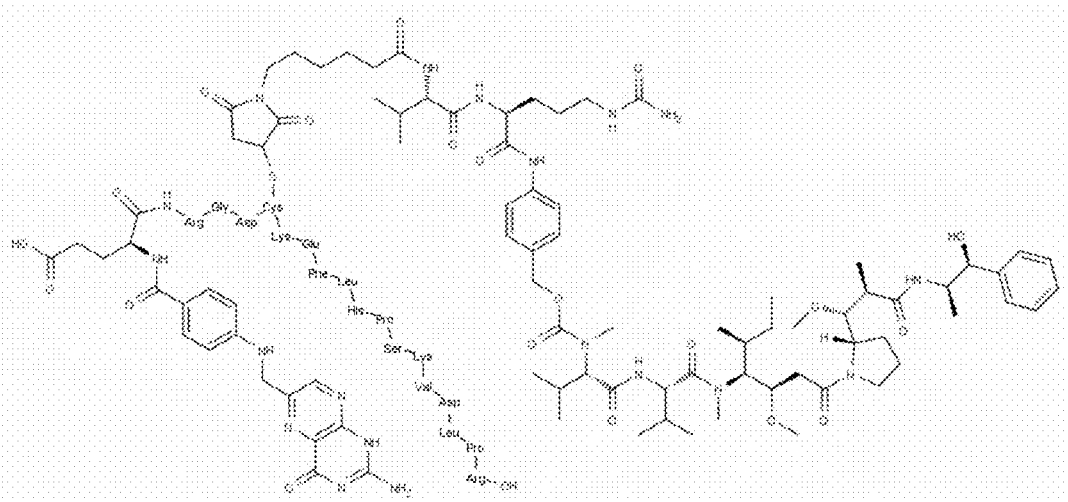
Figure 1:
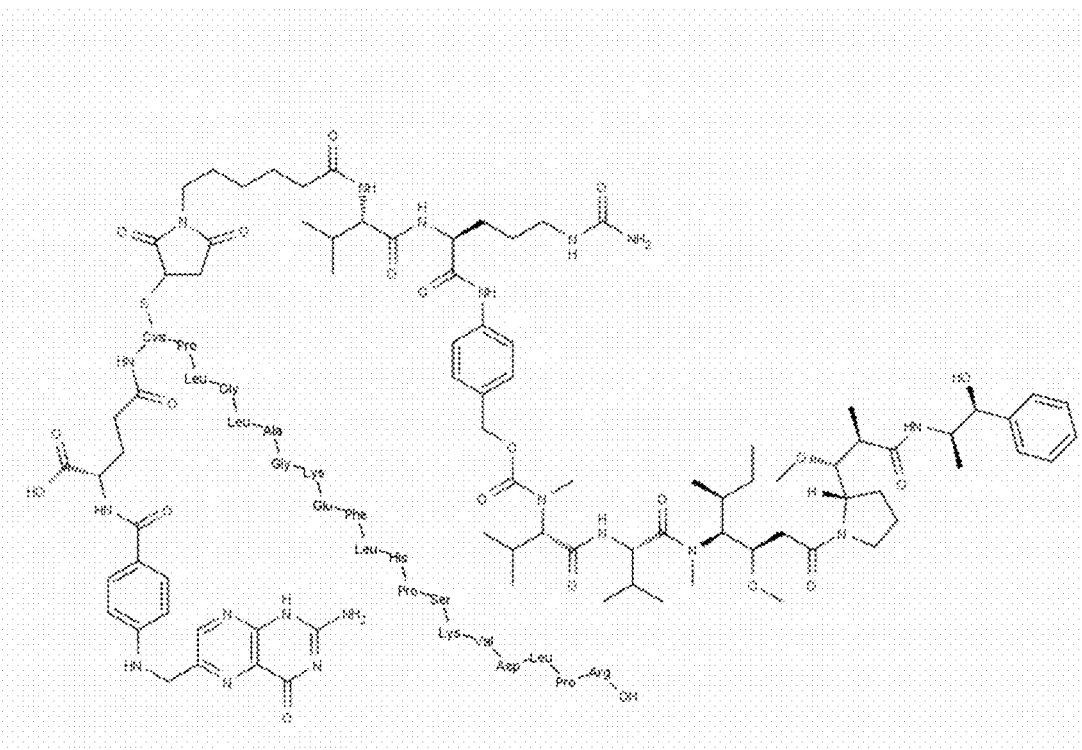
Figure 1:
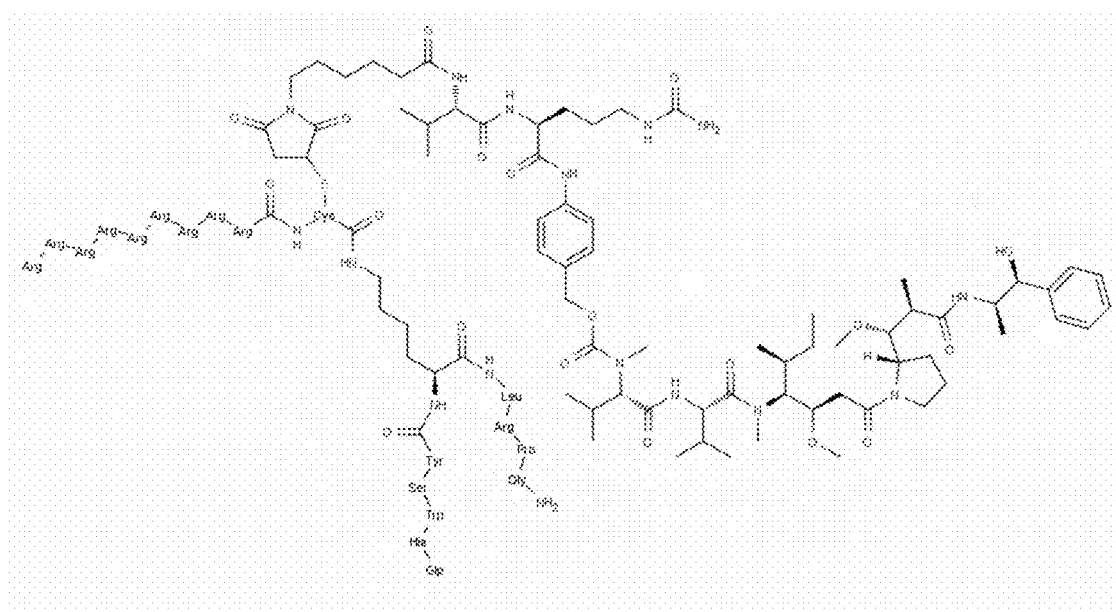

While various aspects and embodiments will be disclosed herein, it is apparent that those skilled in the art may make various equivalent changes and modifications to the aspects and embodiments without deviating from the subject spirit and scope of the present application. The various aspects and embodiments disclosed herein are only for the purposes of illustration and are not intended to be limiting, with the true scope being indicated by the appended claims. All publications, patents or patent applications cited herein are incorporated by reference to their entirety. Unless defined otherwise, the technical and scientific terms used herein have the same meanings as commonly understood by a person skilled in the art to which the present application belongs.

As used herein and in the appended claims, the singular forms "a", "an", and "the" include plural reference unless the context clearly dictates otherwise. The terms "a" (or "an"), "one or more" and "at least one" can be used interchangeably herein. It is also to be noted that the terms "comprising", "including", and "having" can be used interchangeably.

One aspect of the present application discloses a conjugate compound or a pharmaceutically acceptable salt thereof, comprising a payload and two or more kinds of cell-interacting molecules, wherein the payload is conjugated with at least one of the cell-interacting molecules.

The term "payload" as used herein refers to a molecule or material to be delivered to a target cell or tissue. Without limitation, the payload may be any pharmaceutical compound that is intended for use in the diagnosis, treatment, or prevention of a disease in a subject.

In some embodiments, the payload is a small molecule compound, a nucleotide (for example, DNA, plasmid DNA, RNA, siRNA, antisense oligonucleotides, aptamers, etc.), a peptide, a protein (for example, enzymes), or a nanoparticle. In some embodiments, the payload is a small molecule compound. In some embodiments, the small molecule compound is selected from the group consisting of maytansine and any derivatives thereof, taxinol and any derivatives thereof, auristatins and any derivatives thereof, epothilones and any derivatives thereof, bleomycin and any derivatives thereof, dactinomycin and any derivatives thereof, plicamycin and any derivatives thereof, and miromycin C. In some embodiments, the payload is auristatins or any derivatives thereof. In some embodiments, the pharmaceutical compound is a chemotherapeutic agent that is used for relieving or treating cancers.

In some embodiments, the conjugate compound or a pharmaceutically acceptable salt thereof disclosed herein comprises one payload. In some embodiments, the conjugate compound or a pharmaceutically acceptable salt thereof disclosed herein comprises at least one payload. For example, the conjugate compound or a pharmaceutically acceptable salt thereof comprises one, two, three, four, five, six, seven, eight, nine, ten, eleven, twelve, thirteen, fourteen, fifteen, sixteen, seventeen, eighteen, nineteen, twenty or more payloads. In a conjugate molecule containing multiple payloads, each of the payloads may be identical or different from one another. In some embodiments, at least two of the payloads are different from one another.

The term "cell-interacting molecule" as used herein refers to any molecule or moiety that can interact with a target cell or a cell surface receptor of the target cell to trigger or facilitate specific binding of the conjugate molecule containing such cell-interacting molecule to the target cell, endocytosis of the conjugate molecule by the target cell, and/or otherwise causing specific association and retention of the conjugate molecule with the target cell.

The cell-interacting molecules may be small chemical molecules or large biomolecules. In some embodiments, the cell-interacting molecules are antibodies, ligands, or endocytosis molecules. In some embodiments, at least one of the cell-interacting molecules is a ligand capable of binding to a cell surface receptor. In some embodiments, at least one of the cell-interacting molecules is an endocytosis molecule capable of mediating endocytosis.

The ligands as disclosed herein may include a wide variety of chemical or biological entities that may have a specific binding affinity to a selected target, e.g. a cell surface receptor, cell, tissue, organ, etc. In some embodiments, the ligand may specifically bind to a protein or marker expressed on the surface of target cells. In some embodiments, the ligands of the present application bind to cell surface receptors with an affinity of $10^{-6}$~$10^{-9}$ (Kd value). In some embodiments, the ligands bind to cell surface receptors with an affinity of at least $10^{-7}$, at least $10^{-8}$, at least $10^{-9}$ M (Kd value). In some embodiments, the ligands of the present application bind to cell surface receptors with an affinity that is at least two, three, four or more times higher for the target cell surface receptor than for other non-targeted cell surface proteins or markers.

In some embodiments, the two or more kinds of cell-interacting molecules of the present application are two or more kinds of ligands that are capable of specifically binding to different cell surface receptors. In some embodiments, the conjugate compound or a pharmaceutically acceptable salt thereof of the present application contains two ligands, wherein the first ligand is capable of specifically binding to a first cell surface receptor, and the second ligand is capable of specifically binding to a second cell surface receptor. In some embodiments, the conjugate molecule contains two ligands, wherein the first ligand is capable of specifically binding to a folate receptor, the second ligand is capable of specifically binding to a luteinizing hormone releasing hormone (LHRH) receptor. In some embodiments, the conjugate molecule contains three ligands, wherein the first ligand is capable of specifically binding to a folate receptor, the second ligand is capable of specifically binding to a LHRH receptor, and the third ligand is capable of specifically binding to a SST-14 receptor.

In some embodiments, the conjugate compound or a pharmaceutically acceptable salt thereof disclosed herein comprises two, three, four, five, six, seven, eight, nine, ten, eleven, twelve, thirteen, fourteen, fifteen, sixteen, seventeen, eighteen, nineteen, twenty, or more cell-interacting molecules. In a conjugate molecule, each of the cell-interacting molecules may be identical or different from one another. In some embodiments, at least two of the cell-interacting molecules are different from one another. In some embodiments, each of the cell-interacting molecules is different from one another.

In some embodiments, a conjugate molecule provided herein comprises only a single payload conjugated with multiple cell-interacting molecules. In some embodiments, a conjugate molecule provided herein comprises multiple payloads conjugated with multiple cell-interacting molecules.

The term "conjugated" as used herein refer to the linking through a covalent bond of two chemical groups, either directly forming a covalent bond between the two chemical groups, or indirectly linking the two chemical groups through a linker.

In some embodiments, the conjugate compound or a pharmaceutically acceptable salt thereof comprises a payload and two or more kinds of cell-interacting molecules, wherein the payload is covalently linked to at least one of the cell-interacting molecules directly. In some embodiments, the payload is covalently linked to each of the cell-interacting molecules directly.

In some embodiments, the conjugate compound or a pharmaceutically acceptable salt thereof comprises a payload and two or more kinds of cell-interacting molecules, wherein the payload is covalently linked to at least one of the cell-interacting molecules through a linker. In some embodiments, the payload is covalently linked to each of the cell-interacting molecules through a linker.

The term "linker" as used herein refers to a molecule or moiety that covalently links a payload to a cell-interacting molecule. The linker includes functional groups for linking to the payload and at least one of the cell-interacting molecules. In some embodiments, the functional groups may include two reactive moieties, one for linking to the payload and the other for linking to the cell-interacting molecule. In some embodiments, the functional groups are different from each other. In some embodiments, the functional groups include a group containing a thiol-reacting moiety and an amine-reacting moiety. In some embodiments, the functional groups are identical to each other. In some embodiments, the functional groups are maleimide groups.

In some embodiments, the linkers of the present application are multivalent linkers that can bind at least one (for example, one, two, three, four, five, six, seven, eight, nine, ten or more) payload and at least two (for example, two, three, four, five, six, seven, eight, nine, ten or more) cell-interacting molecules. The payloads bound to the multivalent linkers may be identical or different, the cell-interacting molecules bound to the multivalent linkers may be identical or different.

In one aspect, the linkers shall be sufficiently stable to avoid from unintended release of payloads during the blood circulation to increase the effective amount of payloads to the target cells or tissue and avoid toxicity. In another aspect, the linkers shall be able to release the payloads around or within the target cells to efficiently kill the target cells or block the functions of the target cells. In some embodiments, the linker comprises at least one cleavable functional group. Preferably, a cleavable functional group is sufficiently stable outside the target cell, but upon entry into the target cell, is cleaved to release the payload. In some embodiments, the cleavable functional group is cleaved at least 10, 20, 30, 50, 100 times or more efficiently in target cells than in the blood or serum of a subject.

Cleavable linkers may be cleaved by hydrolysis, enzymatic reaction, or reduction reaction, or by pH change. In some embodiments, the linker is cleavable under certain physiological environment, for example, under an appropriate pH environment. In some embodiments, the linker is cleavable in an acidic environment with a pH of about 6.5 or lower, or by agents such as enzymes that can act as a general acid. In some embodiments, the linker is susceptible to cleavage agents, for example, pH, redox potential or the presence of degradative molecules.

In some embodiments, the linker is non-cleavable. Non-cleavable linkers as used herein refer to linkers which remain intact during intracellular metabolism.

In some embodiments, the linker is a peptide linker consisting of a straight or branched chain of amino acids linked by peptide bonds. In some embodiments, the peptide linker is cleavable by protease that is highly or specifically expressed around or in target cells, for example, Cathepsin B in lysosome or endosome. The peptide linkers as used herein can be of varying lengths. Typically, a peptide linker of the present application is from 1 to 50 amino acids in length. In some embodiments, the peptide linker is from 2 to 45, from 2 to 40, from 2 to 35, from 2 to 30, from 2 to 25, from 2 to 20, from 2 to 15, from 2 to 10, from 2 to 9, from 2 to 8, from 2 to 7, from 2 to 6, from 2 to 5, from 2 to 4, from 2 to 3 amino acids in length. The number of amino acids of the peptide linker as described herein can be equal to any integer value within the above numerical range, including the end-points of the range. In some embodiments, the peptide linker is preferred to have a length of two, three, four, or five amino acids in length. In some embodiments, the peptide linker is valine-citruline (Val-Cit), phenylalanine-lysine, or valine-lysine.

In some embodiments, the linker is a disulfide linker containing a disulfide bond. A disulfide bond may be cleaved under intracellular reductive environment, while remains stable in circular system. The disulfide linker of the present application may be DSDM, DMDS, MDS, or NDMDS. The structures of these disulfide linkers are shown in Table 1 below.

TABLE 1

Structures of DSDM, DMDS, MDS and NDMDS

| Name | Structure |
| --- | --- |
| DSDM | 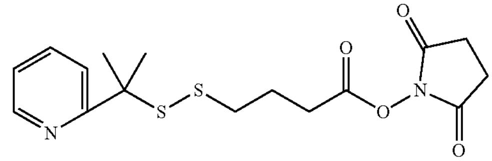 [SMILES: CC(C)(SSCCCC(=O)ON1C(=O)CCC1=O)c1ccccn1] |

TABLE 1-continued

Structures of DSDM, DMDS, MDS and NDMDS

| Name | Structure |
|---|---|
| DMDS | (structure) |
| MDS | (structure) |
| NDMDS | (structure) |

In some embodiments, the linker is a pH-dependent linker. The pH-dependent linker as described herein may be cleavable under certain pH environment. In some embodiments, the pH-dependent linker may be stable under alkaline conditions, while cleavable under acidic conditions, for example, under a pH value of 6.5 or lower. In some embodiments, the pH-dependent linker is cis-aconitic anhydride.

In some embodiments, the linker of the present application comprises any one or combination of the linkers as described above. In some embodiments, the linker of the present application may contain a spacer as a part of the linker.

In some embodiments, the payload is conjugated with a first cell-interacting molecule directly or indirectly, and the first cell-interacting molecule is conjugated with a second cell-interacting molecule directly or indirectly. In some embodiments, the payload is conjugated with each of the first and the second cell-interacting molecule directly. In some embodiments, the payload is conjugated with each of the first and the second cell-interacting molecule indirectly. In some embodiments, the payload is conjugated with the first cell-interacting molecule indirectly, e.g. via a linker, and the first cell-interacting molecule is conjugated with the second cell-interacting molecule directly or indirectly. In some embodiments, the payload is conjugated with the first cell-interacting molecule via a first linker, and the payload is conjugated with the second cell-interacting molecule via a second linker. In some embodiments, the linker is a multivalent linker which binds at least one (for example, one, two, three, four, five, six, seven, eight, nine, ten or more) payload and at least two (for example, two, three, four, five, six, seven, eight, nine, ten or more) ligands. A multivalent linker may also be used to prepare a conjugate molecule comprising multiple payloads and multiple cell-interacting molecules.

In some embodiments, two cell-interacting molecules may be linked to each other via a spacer. In some embodiments, one or more spacers are used to link two, three, four, five, six, seven, eight, nine, ten or more cell-interacting molecules. In some embodiments, the spacer is cleavable by proteases that are specifically expressed by target cells or triggered to be expressed by target cells. Such proteases include, for example, the proteases as listed in Table 2 below. In some embodiments, the spacer comprises the amino acid sequence selected from any one of the amino acid sequences as listed in Table 2 below.

TABLE 2

List of Enzymatically Cleavable Sequences

| Protease | Amino Acid Sequence of Recognition Site | SEQ ID NO. |
|---|---|---|
| Cathepsin B | RR | — |
| Legumain | ASN | — |
| Matripase | KSRAEDE | SEQ ID NO: 1 |
| MMP-2 | PLGLAG | SEQ ID NO: 2 |
| Prostate Specific Antigen | SSLY | SEQ ID NO: 3 |

TABLE 2-continued

List of Enzymatically Cleavable Sequences

| Protease | Amino Acid Sequence of Recognition Site | SEQ ID NO. |
|---|---|---|
| Stromelysin-3 | AAA | — |
| TMPRSS2 | LLRSLIG | SEQ ID NO: 4 |
| Urokinase-typeplasminogen activator | SSR | — |
| Activated Protein C | LVKR | SEQ ID NO: 5 |
| Factor Ixa | LVVR | SEQ ID NO: 6 |
| Factor VIIa | QLTR | SEQ ID NO: 7 |
| Factor Xa | LEGR | SEQ ID NO: 8 |
| Thrombin | PR | — |
| Calpain-a | PLFAEP | SEQ ID NO: 9 |
| Calpain-2 | GLGSEP | SEQ ID NO: 10 |
| Enteropeptidase | DDDDK | SEQ ID NO: 11 |
| MMP-8 | GPSG | SEQ ID NO: 12 |
| Cathepsin L | PLG | — |
| Prpprotein Covertase 5 | RSKR | SEQ ID NO: 13 |
| Calpain-3 | VGVF | SEQ ID NO: 14 |

The terms "cleavable" or "cleaved" as used herein refer to a metabolic process or reaction process on the conjugate compound provided herein, whereby the linker between the payload and the cell-interacting molecule, or the spacer between the cell-interacting molecules are broken to release free payload or cell-interacting molecule. The linker and spacer is either cleaved by proteases or cleaved under certain physiological environment, e.g. pH environment.

In some embodiments, the conjugate compound or a pharmaceutically acceptable salt thereof as described herein contains a payload conjugated with three ligands, wherein the first ligand is capable of specifically binding to a first cell receptor, the second ligand is capable of specifically binding to a second cell receptor, and the third ligand is capable of specifically binding to a third cell surface receptor.

In some embodiments, the third ligand is conjugated with the first ligand directly or indirectly, e.g. via a spacer. In some embodiments, the third ligand is conjugated with the payload directly or indirectly, e.g. via a linker. In some embodiments, the first ligand is conjugated with the second ligand directly or indirectly, e.g. via a spacer, and the second ligand is conjugated with the third ligand directly or indirectly, e.g. via a spacer.

In some embodiments, the first cell surface receptor, the second cell surface receptor and the third cell surface receptor are different from one another, either in structures or functions. In some embodiments, at least two of the first cell surface receptor, the second cell surface receptor, and the third cell surface receptor are different from one another, either in structures or functions. In some embodiments, the first ligand, the second ligand, and the third ligand are the same.

In some embodiments, the conjugate molecule has the structures of Formula I, II, III, IV, V, VI, VII, VIII, IX or X shown below, wherein n, m, p, q, r and s are independently 0 or 1, which represent that the linker and spacer are present or absent independently.

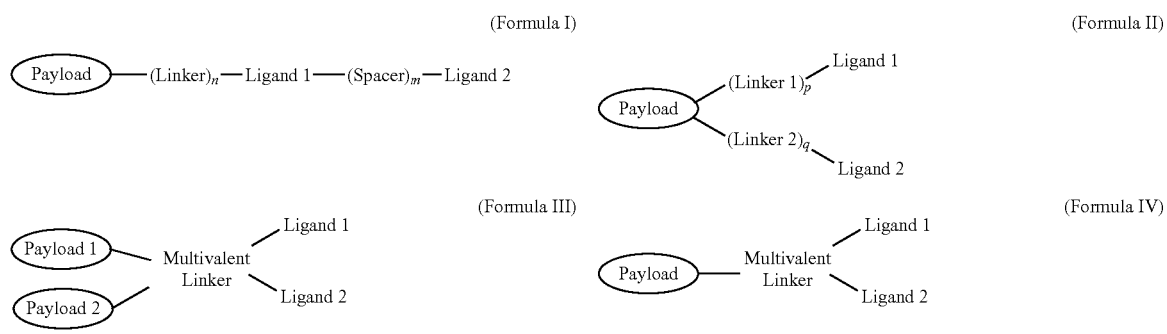

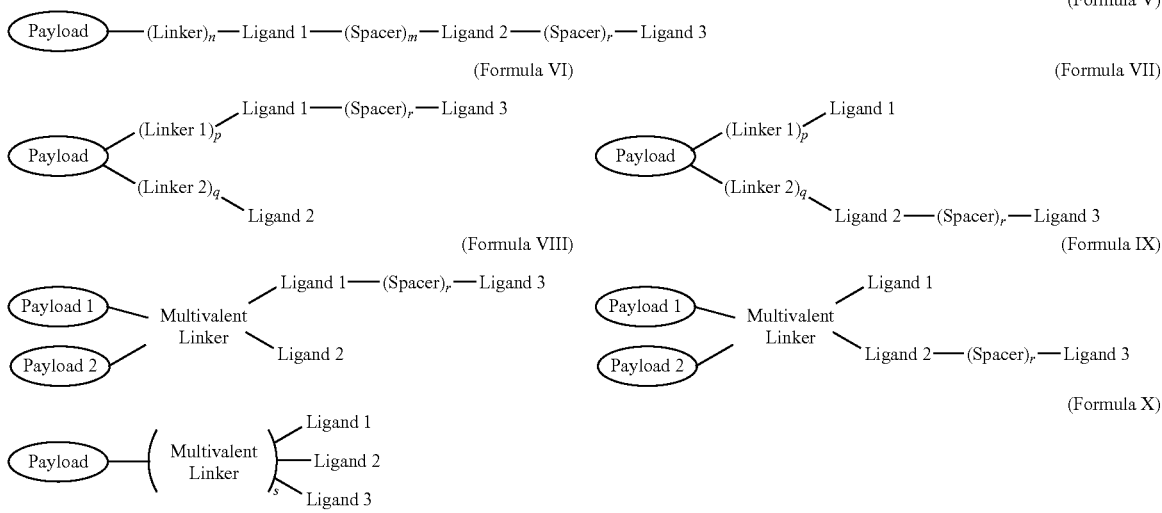

In preferred embodiments, the expressions of the cell surface receptors are significantly higher in target cells (e.g. cancer cells) than in normal cells. The term "significantly" as used herein refers to statistically significant differences, or significant differences that can be recognized by a person skilled in the art.

In some embodiments, the expression levels of the cell surface receptors is 2-1,000,000 folds higher in target cells (e.g. cancer cells) than in normal cells, for example, 2-10, 2-100, 2-1,000, 2-10,000, 2-100,000, 2-1,000,000 folds (can be equal to any value within the above numerical range, including the end-points of the range) higher in target cells (e.g. cancer cells) than in normal cells. In some embodiments, the expression levels of the cell surface receptors is at least 10 folds higher, or 100 folds higher, or 1,000 folds higher, or 10,000 folds higher, or 100,000 folds higher in target cells (e.g. cancer cells) than in normal cells. In some embodiments, the level of the cell surface receptor on normal cells is reduced by at least 50%, 60%, 70%, 80%, 90%, 95%, or 99% when compared with the level of the cell surface receptor on target cells (e.g. cancer cells). In some embodiments, the cell surface receptors described herein are undetectable on normal cells.

In some embodiments, the first, second and third cell surface receptor is independently selected from the group consisting of a transferrin receptor (TFR), a low-density lipoprotein receptor (LDLR), a folate receptor (FR), a uric acid kinase receptor, a tumor necrosis factor receptor (TNFR), integrin receptor LFA-1, SST-14 receptor, LHRH receptor, TRPV6 receptor, and a protease surface antigen receptor.

In some embodiments, the first ligand, the second ligand, and the third ligand are the same. In some embodiments, at least two of the first ligand, the second ligand, and the third ligand are different from each other. In some embodiments, the first ligand, the second ligand, and the third ligand are capable of specifically binding to the same cell surface receptor. In some embodiments, the first ligand, the second ligand, and the third ligand are capable of specifically binding to different cell surface receptors. In some embodiments, each of the first ligand, the second ligand, and the third ligand is capable of binding to two or more different cell surface receptors.

In some embodiments, the first ligand, the second ligand, and the third ligand are independently selected from the group consisting of folate and analogs thereof, and a peptide. In some embodiments, the first ligand, the second ligand, and the third ligand are independently folate or analogs thereof, and at least two of the ligands are different from one another. In some embodiments, the analogs of folate is selected from the group consisting of 5-methyltetrahydrofolate, 5-formyltetrahydrofolate, sulfanilamide, methotrexate, and 5,10-methylenetetrahydrofolate.

In some embodiments, the first ligand, the second ligand, and the third ligand are independently peptides. In some embodiments, the peptide comprises the amino acid sequence selected from the group consisting of SEQ ID NO: 15, SEQ ID NO: 16, SEQ ID NO: 17, SEQ ID NO: 18, RGD, a homologous peptide having at least 70%, at least 80%, at least 85%, at least 90%, at least 91%, at least 92%, at least 93%, at least 94%, at least 95%, at least 96%, at least 97%, at least 98%, at least 99% amino acid sequence homology to any of SEQ ID NO: 15-18, wherein the homologous peptides are functional equivalents of the peptides of SEQ ID NOs: 15-18, respectively.

The term "percent (%) homology to" as used herein refers to, for amino acid sequences, the percentage of identity between two amino acid sequences after aligning the candidate and the reference sequences, and if necessary introducing gaps, to achieve the maximum number of identical amino acids; for nucleotide sequence, the percentage of identity between two nucleotide sequences after aligning the candidate and the reference sequences, and if necessary introducing gaps, to achieve the maximum number of identical nucleotides.

The percentage of homology can be determined by various well-known methods in the art. For example, the comparison of sequence can be achieved by the following publically available tools: BLASTp software (available from the website of National Center for Biotechnology Information (NCBI) blast.ncbi.nlm.nih.gov/Blast.cgi, also see, Altschul S. F. et al., J. Mol. Biol., 215:403-410 (1990); Stephen F. et al, Nucleic Acids Res., 25:3389-3402 (1997)), ClustalW2 (available from the website of European Bioinformatics Institute: www.ebi.ac.uk/Tools/msa/clustalw2/, also see, Higgins D. G. et al., Methods in Enzymology, 266:383-402 (1996); Larkin M. A. et al., Bioinformatics (Oxford, England), 23(21): 2947-8 (2007)) and Tcoffee (available from the website of Sweden Bioinformatics Institute, also see, Poirot O. et al., Nucleic Acids Res., 31(13): 3503-6 (2003); Notredame C. et al., J. Mol. Boil., 302(1): 205-17 (2000)). If the alignment of the sequences is performed using software, the default parameters available in the software may be used, or otherwise the parameters may be customized to suit the alignment purpose. All of these are within the scope of knowledge of a person skill in the art.

The term "functional equivalent" as used herein refers to a derivative peptide that retains a biological activity that is substantially similar to that of the original peptide sequence that the derivative peptide derives from. A functional equivalent may be a natural derivative or is prepared synthetically. Exemplary functional equivalents include amino acid sequences having substitutions, deletions, or additions of one or more amino acids, provided that the biological activity of the peptide is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

In some embodiments, the functional equivalents include conservative substitution of amino acid residues. The conservative substitution of amino acid residues refers to the substitution between amino acids with similar properties, for example, the substitution between polar amino acids (such as the substitution between glutamine and asparagine), the substitution between hydrophobic amino acids (such as the substitution among leucine, isoleucine, methionine and valine), as well as the substitution between amino acids with identical charges (such as the substitution among arginine, lysine and histidine, or the substitution between glutamic acid and aspartic acid), etc.

In some embodiments, at least one of the cell-interacting molecules of the conjugate compound or a pharmaceutically acceptable salt thereof is an endocytosis molecule capable of mediating endocytosis.

The term "endocytosis molecule" as used herein refers to a molecule that can mediate the endocytosis, internalization, or uptake of the conjugate compound disclosed herein or a pharmaceutically acceptable salt thereof into target cells after such molecule interacts with the target cells.

In some embodiments, the endocytosis molecule is selected from the group consisting of folate and analogs thereof, a peptide capable of mediating endocytosis, and a cell-penetrating peptide.

In some embodiments, the endocytosis molecule is also capable of specifically binding to a cell surface receptor. In some embodiments, the endocytosis molecule provided herein is folate or analogs thereof. In some embodiments, the analogs of folate is selected from the group consisting of 5-methyltetrahydrofolate, 5-formyltetrahydrofolate, sulfanilamide, methotrexate, and 5,10-methylenetetrahydrofolate.

Folate is beneficial for forming chemical bond with the other groups due to its small molecule weight, free of immunogenicity, and good stability. Folate can be associated with folate receptors expressed on cell surface with high affinity to mediate cellular uptake of folate. Although expressed at very low levels in most normal cells, folate receptors are expressed at high levels in numerous cancer cells to meet the high folate demand of rapidly dividing cells under low folate conditions (see Kelemen L E, Int J Cancer, 2006; 119: 243-50; Kane M A, et al., J Clin Invest. 1988; 81: 1398-406; Matsue H, et al., Proc Natl Acad Sci USA. 1992; 89: 6006-9; Zhao R, et al., Annu Rev Nutr. 2011; 31: 177-201). Folate is capable of specifically binding to folate receptors on cell surface, and is also an endocytosis molecule capable of mediating endocytosis of the conjugate compound or a pharmaceutically acceptable salt thereof into target cells.

In some embodiments, the endocytosis molecule is a peptide capable of mediating endocytosis. In some embodiments, the endocytosis molecule is further capable of specifically binding to a cell surface receptor. In some embodiments, the peptide capable of mediating endocytosis comprises the amino acid sequence selected from the group consisting of SEQ ID NO: 16, SEQ ID NO: 17, SEQ ID NO: 18, RGD, a homologous peptide having at least 70%, at least 80%, at least 85%, at least 90%, at least 91%, at least 92%, at least 93%, at least 94%, at least 95%, at least 96%, at least 97%, at least 98%, at least 99% amino acid sequence homology to any of SEQ ID NO: 16-18, wherein the homologous peptides are functional equivalents of the peptides of SEQ ID NOs: 16-18, respectively.

In some embodiments, the endocytosis molecule is a cell-penetrating peptide. Cell-Penetrating Peptides (CPPs), also known as protein transduction domains (PTDs), are short peptides (generally less than 40 amino acids), with the ability to gain access to the interior of cells in a receptor-independent manner. The cell-penetrating peptides, when conjugated to payloads, are capable of mediating the transmembrane transport of the payloads and have the activity of protein transduction. In some embodiments, the cell-penetrating peptides as described herein are selected from the group consisting of a tumor-homing peptide, a mitochondrial penetrating peptide, an activatable cell-penetrating peptide, and an antibacterial peptide. In some embodiments, the cell-penetrating peptide comprises the amino acid sequence selected from the group consisting of SEQ ID NO: 19 (RRRRRRRRR, named as R9) and SEQ ID NO: 20 (GRKKRRQRRRPPQ, which is a Tat peptide, i.e. the cell-penetrating peptide of the HIV transactivator of transcription protein).

In some embodiments, the peptide capable of mediating endocytosis as described herein has conservative substitution of amino acids at only one amino acid site compared to the sequences of SEQ ID NOs: 16-20, RGD. In some embodiments, the peptide capable of mediating endocytosis as described herein has conservative substitution of amino acids at 2, 3, 4, 5, 6, 7, 8, 9, or 10 amino acid sites compared to the sequences of SEQ ID NOs: 16-20.

On the pre-condition of not affecting its biological activity, the peptide capable of mediating endocytosis as described herein may also contain non-naturally occurring amino acids, including, for example, β-fluoro-alanine, 1-methyl-histidine, γ-methylene-glutamic acid, α-methyl-leucine, 4,5-dehydro-lysine, hydroxyproline, 3-fluoro-phenylalanine, 3-amino-tyrosine, 4-methyl-tryptophan, and the like.

In some embodiments, the conjugate compound provided herein or a pharmaceutically acceptable salt thereof comprises at least one (for example, one, two, three, four, five, six, seven, eight, nine, ten and more) payload as provided herein, at least one (for example, one, two, three, four, five, six, seven, eight, nine, ten and more) ligand as provided herein, at least one (for example, one, two, three, four, five, six, seven, eight, nine, ten and more) endocytosis molecule as provided herein, and optionally a linker or spacer as provided herein. In some embodiments, the conjugate compound provided herein or a pharmaceutically acceptable salt thereof comprises one payload as provided herein, one ligand as provided herein, one endocytosis molecule as provided herein, and optionally a linker or spacer as provided herein.

In some embodiments, the conjugate compound has the structures of Formula XI, XII, XIII, XIIII, or XV shown as follows, wherein n, m, p, q and s are independently 0 or 1, which represent that the linker, multivalent linker and spacer are present or absent independently.

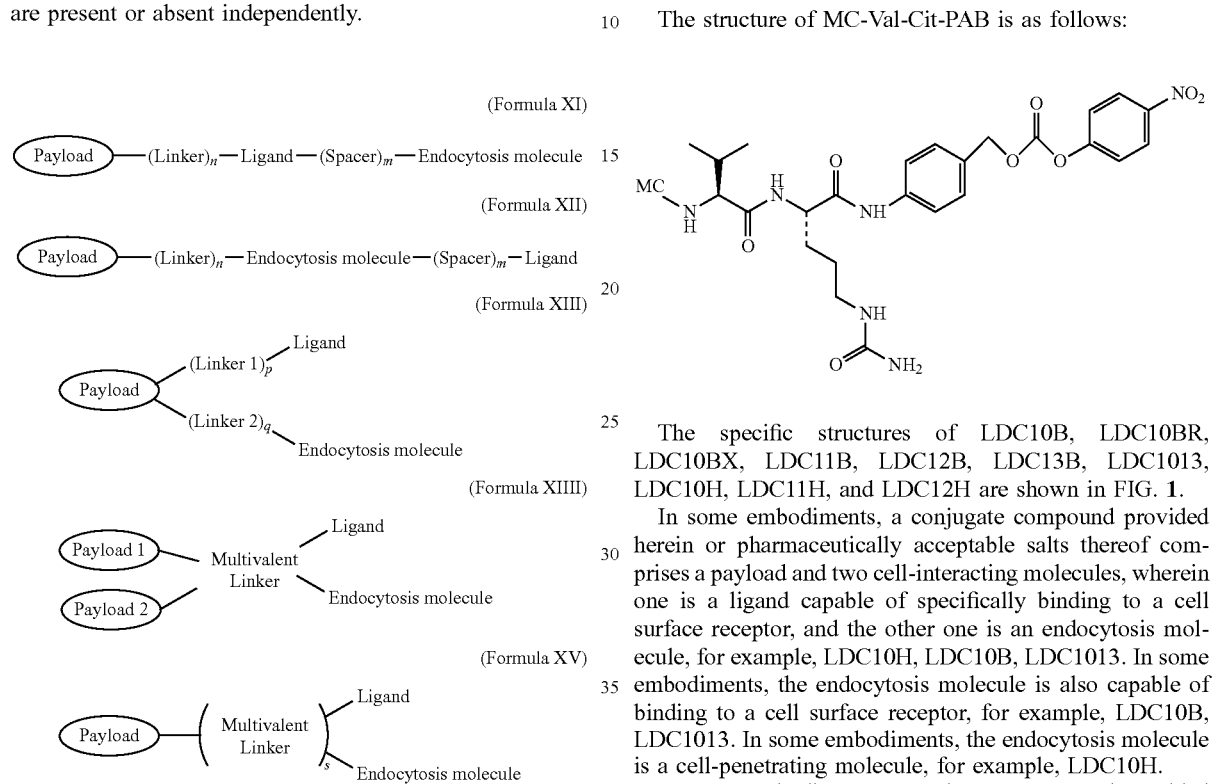

In some embodiments, the conjugate compound of the present application is selected from the group consisting of the following compounds: LDC10B, LDC10BR, LDC10BX, LDC11B, LDC12B, LDC13B, LDC1013, LDC10H, LDC11H, LDC12H, LDC13H. The components of LDC10B, LDC10BR, LDC10BX, LDC11B, LDC12B, LDC13B, LDC1013, LDC10H, LDC11H, and LDC12H are shown in Table 3 below.

TABLE 3

Components of Conjugate Compounds

| Name of Conjugate Compound | Cell-interacting Molecules | Linker | Payload |
|---|---|---|---|
| LDC10B | Folate; P10 | MC-Val-Cit-PAB | MMAE |
| LDC10BR | Folate; P10; RGD | MC-Val-Cit-PAB | MMAE |
| LDC10BX | Folate; P10 | MC-Val-Cit-PAB | MMAE |
| LDC11B | Folate; P11 | MC-Val-Cit-PAB | MMAE |
| LDC12B | Folate; P12 | MC-Val-Cit-PAB | MMAE |
| LDC13B | Folate; P13 | MC-Val-Cit-PAB | MMAE |
| LDC1013 | P10; P13 | MC-Val-Cit-PAB | MMAE |
| LDC10H | R9; P10 | MC-Val-Cit-PAB | MMAE |
| LDC11H | R9; P11 | MC-Val-Cit-PAB | MMAE |
| LDC12H | R9; P12 | MC-Val-Cit-PAB | MMAE |
| LDC13H | R9; P13 | MC-Val-Cit-PAB | MMAE |

The structure of MC-Val-Cit-PAB is as follows:

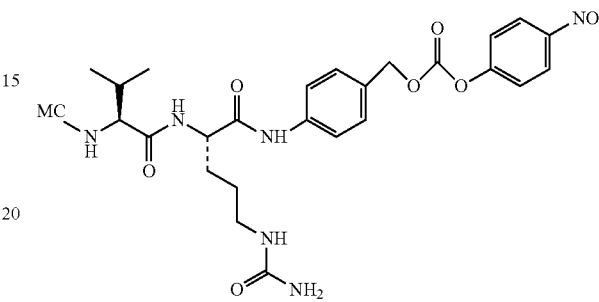

The specific structures of LDC10B, LDC10BR, LDC10BX, LDC11B, LDC12B, LDC13B, LDC1013, LDC10H, LDC11H, and LDC12H are shown in FIG. 1.

In some embodiments, a conjugate compound provided herein or pharmaceutically acceptable salts thereof comprises a payload and two cell-interacting molecules, wherein one is a ligand capable of specifically binding to a cell surface receptor, and the other one is an endocytosis molecule, for example, LDC10H, LDC10B, LDC1013. In some embodiments, the endocytosis molecule is also capable of binding to a cell surface receptor, for example, LDC10B, LDC1013. In some embodiments, the endocytosis molecule is a cell-penetrating molecule, for example, LDC10H.

In some embodiments, a conjugate compound provided herein or pharmaceutically acceptable salts thereof comprises a payload and two cell-interacting molecules, which are both endocytosis molecules, for example, LDC11B, LDC12B, LDC13B. In some embodiments, a conjugate compound provided herein or pharmaceutically acceptable salts thereof comprises a first endocytosis molecule and a second endocytosis molecule, wherein the first endocytosis molecule is the same as the second endocytosis molecule. In some embodiments, a conjugate compound provided herein or pharmaceutically acceptable salts thereof comprises a first endocytosis molecule and a second endocytosis molecule, wherein the first endocytosis molecule is different from the second endocytosis molecule, for example, LDC11B, LDC12B, LDC13B. In some embodiments, a conjugate compound provided herein or pharmaceutically acceptable salts thereof comprises a payload and two cell-interacting molecules, which are both endocytosis molecules also capable of specifically binding to cell surface receptors, for example, LDC11B, LDC12B, LDC13B. In some embodiments, the first endocytosis molecule is also capable of specifically binding to a cell surface receptor, and the second endocytosis molecule is a cell penetrating molecule, for example, LDC11H, LDC12H, LDC13H.

In some embodiments, a conjugate compound provided herein or pharmaceutically acceptable salts thereof comprises a payload and two cell-interacting molecules, which are both ligands capable of specifically binding to cell surface receptors. In some embodiments, a conjugate compound provided herein or pharmaceutically acceptable salts thereof comprises a first cell-interacting molecule capable of binding to a first cell surface receptor and a second cell-interacting molecule capable of binding to a second cell surface receptor, wherein the first cell-interacting molecule is the same as the second cell-interacting molecule. In some embodiments, a conjugate compound provided herein or pharmaceutically acceptable salts thereof comprises a first cell-interacting molecule capable of binding to a first cell surface receptor and a second cell-interacting molecule capable of binding to a second cell surface receptor, wherein the first cell-interacting molecule is different from the second cell-interacting molecule, for example, LDC10B, LDC11B, LDC12B, LDC13B, LDC1013.

The mLDC of the present application may be used for specifically delivering any payload to target cells in the target tissue environment. Generally, the advantage of multiple ligands in mLDC are threefold. Firstly, multiple ligands can act in multiple modes, often synergistically, resulting in improved therapeutic effect while reducing side effects. Secondly, multiple-ligand binding increases the affinity and avidity of a mLDC towards target receptors or target cells, therefore enhancing its specificity and avoiding off target toxicity. Finally, when properly designed, the combination of multiple ligands can fulfill the multi-function requirement often called for drug conjugate.

The mLDC of the present application achieves unexpected technical effects, including but are not limited to: (1) the combination of ligand capable of binding to cell surface receptors and endocytosis molecule enable the conjugate compound specifically entering into target cells; (2) mLDC enhances the affinity and targeting specificity of the drug compounds so as to deliver highly effective chemotherapeutic agents such as MMAE to the patient, to broaden the therapeutic window of such agents and avoid side effects; (3) the linker can prevent release of the payload outside of the target cells (for example, blood circulation system, intercellular substance, etc.), which ensures the stability of the conjugate compound during the blood circulation, and reduce the toxicity of the drug. After entering into target cells, the linker is cleaved to release the payload to exert the effect of the drug. Meanwhile, it is possible to avoid multiple drug resistance (MDR); (4) a wide variety of drugs may be delivered in the form of the conjugate compounds of the present application and therefore widens the scope of applications of the relevant drugs. Therefore, mLDCs of the present application not only broaden the targeting scope and therapeutic window of LDC drugs, but also reduce toxicity and side effects of some drugs.

For example, dual ligands may be used in a conjugate wherein one ligand specifically binds to a cancer cell surface receptor, while the other ligand, unmasked only inside a solid tumor by cancer specific proteases, triggers endocytosis allowing the conjugate to specifically deliver the drug payload to only cancer cells, avoiding toxicity towards normal cells expressing either or both receptor(s).

For example, LDC10B containing two ligands, P10 peptide and folate, can function in dual mode and even triple mode. P10 peptide itself has been shown in Phase I trial to be an effective cancer drug, working perhaps as a TRPV6 antagonist and folate has been shown to help deliver cytotoxin payloads efficiently through endocytosis to kill cancer cells. As a dual-ligand drug conjugate, LDC10B can potentially function synergistically in the following three ways to kill cancer cells expressing both TRPV6 and Folate receptors. Firstly, the P10 peptide part functions itself as a TRPV6 antagonist. Secondly, P10 peptide can potentially deliver the conjugated cytotoxin via internalization, although not very efficient; and folate can bind to folate receptor to deliver cytotoxins efficiently through endocytosis. Finally, the dual ligands, P10 peptide and folate could bind synergistically to their respective receptors and deliver the cytotoxin payload to inside of target cells expressing both receptors.

The terms "polypeptide", "protein" and "peptide" as used herein can be used interchangeably and refer to the polymer of amino acids. The polypeptide, protein or peptide as described herein may contain naturally-occurring amino acids, as well as non-naturally-occurring amino acids, or analogues and simulants of amino acids. The polypeptide, protein or peptide can be obtained by any method well-known in the art, for example, but not limited to, isolation and purification from natural materials, recombinant expression, chemical synthesis, etc.

Another aspect of the present application discloses pharmaceutical compositions comprising the conjugate compounds provided herein, or pharmaceutically acceptable salts thereof, and pharmaceutically acceptable carriers.

The term "pharmaceutically acceptable" as used herein means it is, within the scope of sound medical judgment, suitable for use in contact with the cells of humans and other animals without undue toxicity, irritation, allergic response, and the like, and are commensurate with a reasonable benefit/risk ratio.

The term "pharmaceutically acceptable salts" as used herein refer to the relatively non-toxic, inorganic and organic acid addition salts, and base addition salts, of the conjugate compounds of the present application. Representative acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates, and quinateslaurylsulphonate salts, and the like. Base addition salts include pharmaceutically acceptable metal and amine salts. Suitable metal salts include the sodium, potassium, calcium, barium, zinc, magnesium, and aluminum salts. In some embodiments, the sodium and potassium salts are preferred. Suitable inorganic base addition salts are prepared from metal bases which include, for example, sodium hydride, sodium hydroxide, potassium hydroxide, calcium hydroxide, aluminum hydroxide, lithium hydroxide, magnesium hydroxide, and zinc hydroxide. Suitable amine base addition salts are prepared from amines which have sufficient basicity to form a stable salt, and preferably include the following amines which are frequently used in medicinal chemistry because of their low toxicity and acceptability for medical use: ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The term "pharmaceutically acceptable carriers" as used herein refer to pharmaceutically acceptable solvents, suspending agents or any other pharmacologically inert vehicles for delivering the conjugate compounds provided herein to subjects, which do not interfere with the structures and properties of the conjugate compounds. Certain of such carriers enable the conjugate compounds to be formulated as, for example, tablets, pills, capsules, liquids, gels, syrups, slurries, suspensions and pastilles, for oral ingestion by subjects. Certain of such carriers can enable the conjugate compounds to be formulated as injections, infusions or local administration.

The pharmaceutically acceptable carriers for use in the pharmaceutical compositions provided herein may include, but are not limited to, for example, pharmaceutically acceptable liquids, gels, or solid carriers, aqueous vehicles (such as sodium chloride injection, Ringer's injection, isotonic dextrose injection, sterile water injection, or dextrose and lactated Ringer's injection), nonaqueous vehicles (such as fixed oils of vegetable origin, cottonseed oil, corn oil, sesame oil, or peanut oil), antimicrobial agents, isotonic agents (such as sodium chloride or dextrose), buffers (such as phosphate or citrate buffers), antioxidants (such as sodium bisulfate), anesthetics (such as procaine hydrochloride), suspending/dispending agents (such as sodium carboxymethylcellulose, hydroxypropyl methylcellulose, or polyvinylpyrrolidone), chelating agents (such as EDTA (ethylenediamine tetraacetic acid) or EGTA (ethylene glycol tetraacetic acid)), emulsifying agents (such as Polysorbate 80 (TWEEN-80)), diluents, adjuvants, excipients, or non-toxic auxiliary substances, other components known in the art, or various combinations thereof. Suitable components may include, for example, fillers, binders, buffers, preservatives, lubricants, flavorings, thickeners, coloring agents, or emulsifiers.

In some embodiments, the pharmaceutical compositions are injection formulations. The injection formulations include sterile water solutions or dispersions, suspensions or emulsions. In all cases, the injection formulations should be sterile and shall be fluid for easy injection. It should be stable under the conditions of manufacture and storage and must be preserved against the contaminating action of microorganisms such as bacteria and fungi. The carriers can be solvents or dispersion medium containing, for example, water, ethanol, polyol (for example, glycerol, propylene glycol, and liquid polyethylene glycol, and the like), and suitable mixtures thereof and/or vegetable oils. The injection formulations should maintain appropriate fluidity. The appropriate fluidity can be maintained, for example, by the use of coatings such as lecithin, by the use of surfactants, and the like. Prevention of the action of microorganisms can be achieved by various antibacterial and antifungal agents, for example, parabens, chlorobutanol, phenol, sorbic acid, thimerosal, and the like.

In some embodiments, the pharmaceutical compositions are oral formulations. The oral formulations include, but are not limited to, capsules, cachets, pills, tablets, lozenges (using a flavored basis, usually sucrose and acacia or tragacanth), powders, granules, or as solutions or suspensions in aqueous or non-aqueous liquids, or as oil-in-water or water-in-oil liquid emulsions, or as elixirs or syrups, or as pastilles (using an insert base, such as gelatin and glycerin, or sucrose and acacia) and/or as mouth washes and the like.

In solid dosage forms for oral administration (e.g., capsules, tablets, pills, dragees, powders, granules and the like), the conjugate compounds are mixed with one or more pharmaceutically acceptable carriers, such as sodium citrate or dicalcium phosphate, and/or any of the followings: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as acetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents.

In liquid dosage forms for oral administration, the conjugate compounds are mixed with any of the followings: pharmaceutically acceptable emulsions, microemulsions, solutions, suspensions, syrups and elixirs. In addition to the conjugate compounds, the liquid dosage forms may contain inert diluents commonly used in the art, such as, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, olive, castor and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

In some embodiments, the pharmaceutical compositions are mouth spray formulations or nasal spray formulations. The spray formulations include, but not limited to, aqueous aerosols, nonaqueous suspensions, lipidosome formulations or solid granular preparations, and the like. Aqueous aerosols are prepared by mixing aqueous solutions or suspensions of agents and conventional pharmaceutically acceptable carriers and stabilizers. The carriers and stabilizers are changed according to the requirements of specific compounds, but in general, they include nonionic surfactants (Tweens or polyethylene glycol), oleic acid, lecithin, amino acids such as glycine, buffer solution, salts, sugar or sugar alcohol. Aerosols are generally prepared by isotonic solutions, and can be delivered by sprayers.

In some embodiments, the pharmaceutical composition can be used by mixing with one or more other drugs. In some embodiments, the pharmaceutical composition comprises at least one other drug. In some embodiments, the other drugs are antineoplastic drugs, cardiovascular drugs, anti-inflammatory drugs, antiviral drugs, digestive system drugs, nervous system drugs, respiratory system drugs, immune system drugs, dermatologic drugs, metabolic drugs, and the like.

In some embodiments, the pharmaceutical compositions can be administered to subjects in need thereof by appropriate routes, including without limitation, oral, injection (such as intravenous, intramuscular, subcutaneous, intracutaneous, intracardiac, intrathecal, intrapleural, intraperitoneal injection, and the like), mucosal (such as nasal, intraoral administration, and the like), sublingual, rectal, percutaneous, intraocular, and pulmonary administration. In some embodiments, the drug compositions can be administered intravenously, subcutaneously, orally, intramuscularly or intraventricularly.

Due to the properties of some payloads, for example, high toxicity, high hydrophilicity, it is desired to deliver the payloads more specifically and more efficiently to the subjects in need thereof. For example, in cancer treatment, it is desired to deliver the chemotherapeutic agents to the cancer cells specifically, without toxicity to normal cells. Therefore, another aspect of the present application discloses methods for delivering a payload to a subject in need thereof, comprising administering to the subject a therapeutically effective amount of the conjugate compounds provided herein, or pharmaceutically acceptable salts thereof, or the pharmaceutical compositions provided herein. The payload described herein may be any pharmaceutical agent that elicits the biological or medicinal response in a tissue, system, animal, individual or human that is being sought by a researcher, veterinarian, medical doctor or other clinicians in preventing, inhibiting, ameliorating or treating a disease.

The term "subject" as used herein refers to human and non-human animals. Non-human animals include all vertebrates, for example, mammals and non-mammals. The subject may also be a livestock animal such as, cattle, swine, sheep, poultry and horse, or domestic animal such as dog and cat. The subject may be male or female, may be elderly, and may be an adult, adolescent, child, or infant. A human subject may be Caucasian, African, Asian, Semitic, or other racial backgrounds, or a mixture of such racial backgrounds.

The term "therapeutically effective amount" as used herein refers to the amount of the conjugate compounds, or pharmaceutically acceptable salts thereof, or pharmaceutical compositions which relieves to some extent one or more symptoms of a disease or disorder in a subject; returns to normal either partially or completely one or more physiological or biochemical parameters associated with or causative of the disease or disorder; and/or reduces the likelihood of the onset of the disease or disorder. Such amounts generally vary according to a number of factors well within the purview of ordinarily skilled artisans given the description provided herein to determine and account for. These include, without limitation: the particular subject, as well as its age, weight, height, general physical condition, and medical history, the particular compound used, as well as the carrier in which it is formulated and the route of administration selected for it; and, the nature and severity of the condition being treated.

In some embodiments, the amounts of the conjugate compounds, or pharmaceutically acceptable salts thereof, or the pharmaceutical compositions are sufficient to inhibit a disease or disorder in a subject, or prophylactically inhibit or prevent the onset of a disease or disorder. Although the therapeutically effective amount may vary in different subjects, it is generally ranged from 0.01 to 100 mg/kg, for example, 0.01 to 90 mg/kg, 0.01 to 80 mg/kg, 0.01 to 70 mg/kg, 0.01 to 60 mg/kg, 0.01 to 50 mg/kg, 0.01 to 40 mg/kg, 0.01 to 30 mg/kg, 0.01 to 20 mg/kg, 0.01 to 10 mg/kg, 0.01 to 5 mg/kg, 0.01 to 4 mg/kg, 0.01 to 3 mg/kg, 0.01 to 2 mg/kg, 0.01 to 1 mg/kg, 0.01 to 0.1 mg/kg. The therapeutically effective amount as described herein can be equal to any value within the above numerical range, including the end-points of the range.

Another aspect of the present application discloses a method for delivering a payload to a subject in need thereof, comprising administering to the subject a therapeutically effective amount of the conjugate compounds provided herein or a pharmaceutically acceptable salt thereof, or the pharmaceutical composition provided herein.

Another aspect of the present application discloses methods for treating a disease in a subject, comprising administering to the subject a therapeutically effective amount of the conjugate compounds provided herein, or pharmaceutically acceptable salts thereof, or the pharmaceutical compositions provided herein.

In some embodiments, the disease is a cancer, including but is not limited to, breast cancer, lung cancer, prostatic cancer, renal cancer, ovarian cancer, gastric cancer, uterine cancer, endometrial carcinoma, liver cancer, thyroid cancer, pancreatic cancer, colon cancer, colorectal cancer, esophageal cancer, skin cancer, lymphoma, leukemia, and multiple myeloma.

In some embodiments, the disease is an immunological disease, for example, an autoimmune disease, including but is not limited to, connective tissue disease, systemic sclerosis, rheumatoid arthritis, and systemic Lupus erythematosus.

In some embodiments, the disease is a cardiovascular disease, including but is not limited to, angina, myocardial infarction, stroke, hypertensive heart disease, including but is not limited to, angina, myocardial infarction, stroke, heart attack, hypertensive heart disease, rheumatic heart disease, cardiomyopathy, heart arrhythmia, and congenital heart disease.

In some embodiments, the disease is a metabolic disease, including but is not limited to, diabetes, gout, obesity, hypoglycemia, hyperglycemia, and dyslipidemia.

In some embodiments, the disease is a neurological disease, including but is not limited to, Alzheimer's disease, Parkinson's disease, Huntington's disease, head injury, multiple sclerosis, vertigo, coma, and epilepsy.

In some embodiments, the method provided herein further comprises administering one or more therapeutic agents in combination with the conjugate compound, or a pharmaceutically acceptable salt thereof, or the pharmaceutical composition. In some embodiments, the therapeutic agent targets an anti-cancer therapeutic target, induces or boosts immune response against cancer, or is a chemotherapeutic agent.

The present application will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

EXAMPLES

The following examples are intended to further illustrate the present application. The advantages and features of the present application will become clear with the descriptions. However, these illustrations are merely exemplary, and should not be constructed as limitations to the scope of the present application.

Example I

Preparation of Conjugate Molecules

Step I: Synthesis of Folate-NHS

Folate (44.1 g, 100 mmol) was dissolved in DMSO (2 L), and then mixed with N,N'-Dicyclohexylcarbodiimide (DCC) (24.8 g, 120 mmol) and N-Hydroxysuccinimide (NHS) (23 g, 200 mmol). The mixture was stirred for 18 h at normal temperature in the dark. The undissolved substances were filtrated and dried in vacuo to obtain colloidal solids. The colloidal solids were washed with ice ether for three times, and dried to obtain yellow powders (53.8 g), which can be used for the next reaction without further purification.

Step II: Synthesis of P10 Protected Peptide Resin

Wang Resin (purchased from Sigma-Aldrich, 100 g, degree of substitution: 1.1 mmol/g) was measured and added into a solid phase reaction column, DMF was then added, and followed by swelling with nitrogen gas bubbling for 30 min. In a separate Erlenmeyer flask, Fmoc-Arg (pbf)-OH (142.7 g, 220 mmol), HOBt (35.6 g, 264 mmol) and DMAP (2.7 g, 22 mmol) were measured and dissolved in DMF, and cooled to 0° C. with ice-water bath. DIC (40.8 ml, 264 mmol) was then added and allowed to react for 5 min. The solution was added into the reaction column and reacted for three hours, and then dried with vacuum and washed with DMF for three times.

Acetic anhydride (104 ml) and pyridine (88.5 ml) were dissolved in DMF (500 ml), the mixture was added into the washed resin above, and sealed and allow to sit at room temperature for 5 h, washed with DMF for three times, contracted with methanol, and then the resin was dried to obtain Fmoc-Arg (pbf)-Wang Resin. The degree of substitution was determined to be 0.53 mmol/g.

37.7 g (20 mmol) of Fmoc-Arg (pbf)-Wang Resin (degree of substitution: 0.53 mmol/g) was measured and added into the reaction column, washed with DMF for three times, and swelled with DMF for 30 min. The Fmoc protection group was removed by DBLK, and then washed with DMF for six times. Fmoc-Pro-OH (20.2 g, 60 mmol) and HOBt (9.7 g, 72 mmol) were measured and dissolved in DMF, and cooled to 0° C. with ice-water bath. DIC (11.1 ml, 72 mmol) was then added and allowed to react for 5 min. The solution was added into the reaction column and reacted for two hours, and then DBLK was added to remove Fmoc protection group.

The above procedures were repeated for the addition of each of the amino acids from the C-terminal end to the N-terminal end in the peptide sequence. Fmoc-Leu-OH, Fmoc-Asp(OtBu)-OH, Fmoc-Val-OH, Fmoc-Lys(Boc)-OH, Fmoc-Ser(tBu)-OH, Fmoc-Pro-OH, Fmoc-His(Trt)-OH, Fmoc-Leu-OH, Fmoc-Phe-OH, Fmoc-Glu(OtBu)-OH, Fmoc-Lys(Boc)-OH and Fmoc-Cys(Trt)-OH were conjugated one by one according to the peptide sequence, and then DBLK was added to remove Fmoc protection group. The solution was washed with DMF for six times, contracted with methanol for twice, and dried to obtain P10 protected peptide resin (85.8 g).

Step III: Synthesis of Intermediate Folate-P10 (Folate-Cys-Lys-Glu-Phe-Leu-His-Pro-Ser-Lys-Val-Asp-Leu-Pro-Arg-OH)

Folate-NHS (32.3 g, 60 mmol) was measured and dissolved in DMSO, P10 protected peptide resin (85.8 g) obtained in Step II was added and reacted for 5 min, DIEA (21 ml, 120 mmol) was added dropwise, and the reaction was continued for 4 h at room temperature. The reaction product was washed with DMF for three times, contracted with methanol, and dried in vacuo to obtain full protected peptide resin (320.3 g).

The protected peptide resin (80 g) obtained above was added into a 1000 ml one-neck flask, the cleavage solution (640 ml, TFA:thioanisole:EDT:anisole=90:5:3:2 (volume ratio)) was pre-prepared, added into the flask, and reacted for 2.5 h at room temperature. The resin was filtrated, and washed with TFA (100 ml), the filtrates were combined and added into absolute ether (4500 ml) to separate out yellow solids. The solids were centrifuged, washed with absolute ether, and dried in vacuo to obtain yellow solids (40.6 g). The crude peptide yield was 97.1%, and HPLC purity was 76.3%. The obtained yellow solids were purified by HPLC and freeze-dried to obtain Folate-P10 (28.25 g, purity: 98.6%).

Step IV: Synthesis of Intermediate R9-P10 (Arg-Arg-Arg-Arg-Arg-Arg-Arg-Arg-Arg-Cys-Lys-Glu-Phe-Leu-His-Pro-Ser-Lys-Val-Asp-Leu-Pro-Arg-OH)

A portion of P10 protected peptide resin obtained in Step II was measured, and conjugated according to the peptide sequence of R9 to obtain intermediate R9-P10.

Step V: Synthesis of Intermediate Mc-Val-Cit-PAB-MMAE

MMAE (7.18 g, 10 mmol) was measured and added into a 250 ml three-neck flask, dissolved in anhydrous DMF, and stirred till clear at room temperature under $N_2$ protection. Mc-Val-Cit-PAB-PNP (7.37 g) and HOAt (72 mg, 2 mmol) were added into the solution and reacted for 5 min, and then DIEA (3.5 ml, 20 mmol) was added drop-wise, the reaction was continued for 30 min at room temperature, and then the temperature was increased to 40~50° C. and reacted for 20 h, during which HPLC was used to monitor the reaction. DMF was removed by drying in vacuo, and the product Mc-Val-Cit-PAB-MMAE (10.7 g, purity: 99.3%) was obtained by further HPLC purification.

Step VI: Synthesis of Conjugates LDC10B and LDC10H

Mc-Val-Cit-PAB-MMAE (6.59 g, 5 mmol) obtained in Step V was measured and added into a 5000 ml one-neck flask, 3300 ml of phosphate buffer was added and stirred till clear under PH=7.2. The intermediate Folate-P10 or R9-P10 (10.5 g, 5.02 mmol) was added and reacted for 2 h at room temperature, during which HPLC was used to monitor the reaction. After the reaction was completed, the solution was filtrated, LDC10B (14.53 g, purity: 99.2%, yield: 85.02%) and LDC10H (12.37 g, purity: 98.7%, yield: 81.34%) were obtained by HPLC and freeze-drying.

The conjugates, LDC10BR, LDC10BX, LDC11B, LDC12B, LDC13B, LDC1013, LDC11H, and LDC12H can be obtained by similar procedures.

Step VII: Synthesis of Folate-FITC (FITC-ACP-Lys (Folate)-OH)

Wang Resin (1 g, degree of substitution: 1.1 mmol/g) was measured and added into a solid phase reaction column, DMF was then added, and followed by swelling with nitrogen gas bubbling for 30 min. In a separate Erlenmeyer flask, 2 equivalent molar (eq.) of Fmoc-Lys(Dde)-OH and 2.4 eq. of HOBt and 0.2 eq. of DMAP were measured and dissolved in DMF, and cooled to 0° C. with ice-water bath. 2.4 eq. of DIC was then added and allowed to react for 5 min. The solution was added into the reaction column and reacted for three hours, and then dried with vacuum and washed with DMF for three times.

10 eq. of Acetic anhydride and pyridine each were dissolved in DMF (10 ml), the mixture was added into the washed resin above, and sealed and allow to sit at room temperature for 5 h, washed with DMF for three times, contracted with methanol, and then the resin was dried to obtain Fmoc-LYS(Dde)-Wang Resin. The degree of substitution was determined to be 0.51 mmol/g.

1.3 g of Fmoc-LYS(Dde)-Wang Resin (degree of substitution: 0.51 mmol/g) was measured and added into the reaction column, washed with DMF for three times, and swelled with DMF for 30 min. The Fmoc protection group was removed by DBLK, and then washed with DMF for six times. 2 eq. of Fmoc-6-ACP-OH and 2.4 eq. of HOBt were measured and dissolved in DMF, and cooled to 0° C. with ice-water bath. 2.4 eq. of DIC was then added and allowed to react for 5 min. The solution was added into the reaction column and reacted for two hours, and then DBLK was added to remove Fmoc protection group.

1.5 eq. FITC in DMF was added to the resin, and followed by drop-wise addition of 3 eq. of DIEA. The reaction proceeded for 2 h and the resin was washed three times with DMF.

2% Hydrazine hydrate in DMF was added to the above resin and allowed to react for 15 min. Repeated twice then washed six times with DMF.

Folate-NHS (2 eq.) was measured and dissolved in DMSO, was added to the resin and reacted for 5 mins, DIEA (21 ml, 120 mmol) was added drop-wise, and the reaction was continued for 4 h at room temperature. The reaction product was washed with DMSO and DMF for three times, respectively, contracted with methanol, and dried in vacuo to obtain full protected peptide resin.

Figure 3:
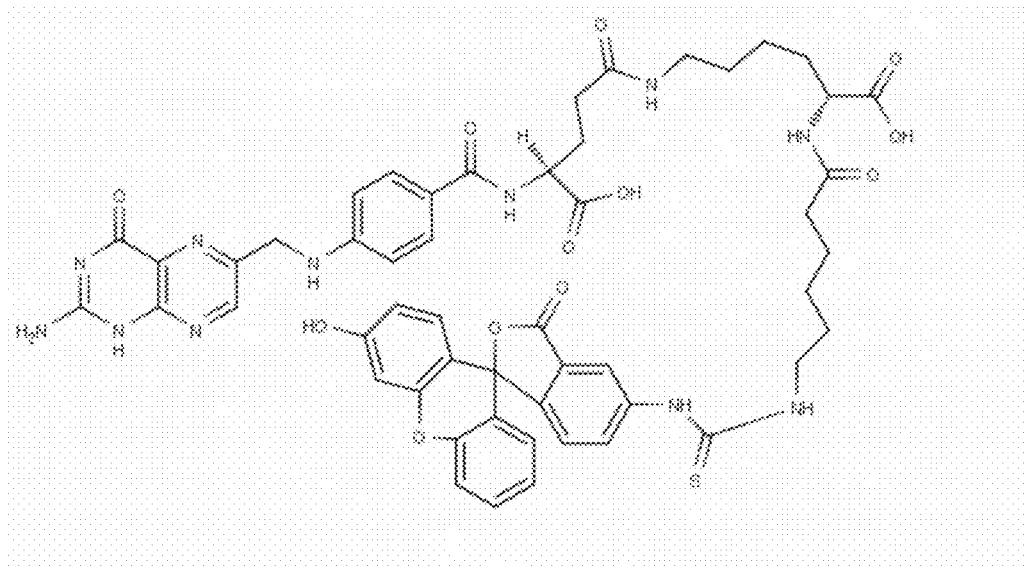
FIG. 3 shows the structures of Folate-FITC, 10A-FITC, and 10B-FITC.
Figure 3:
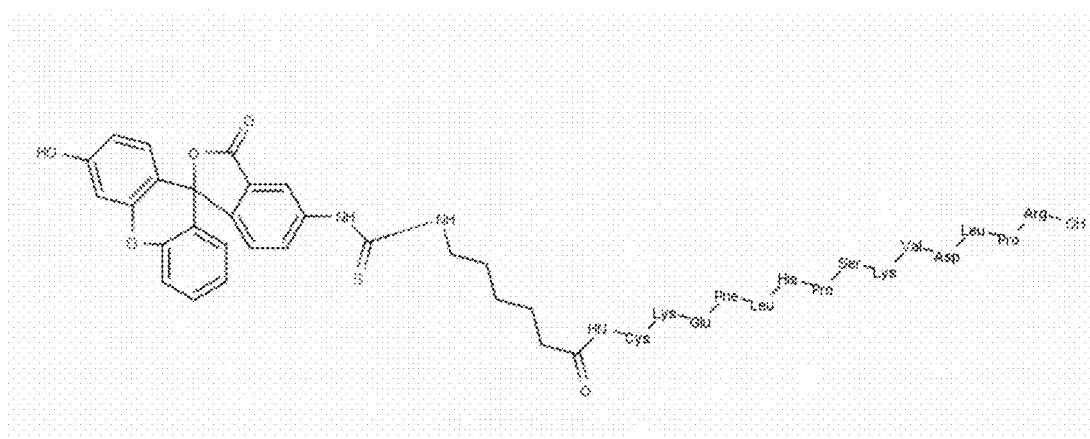
Figure 3:
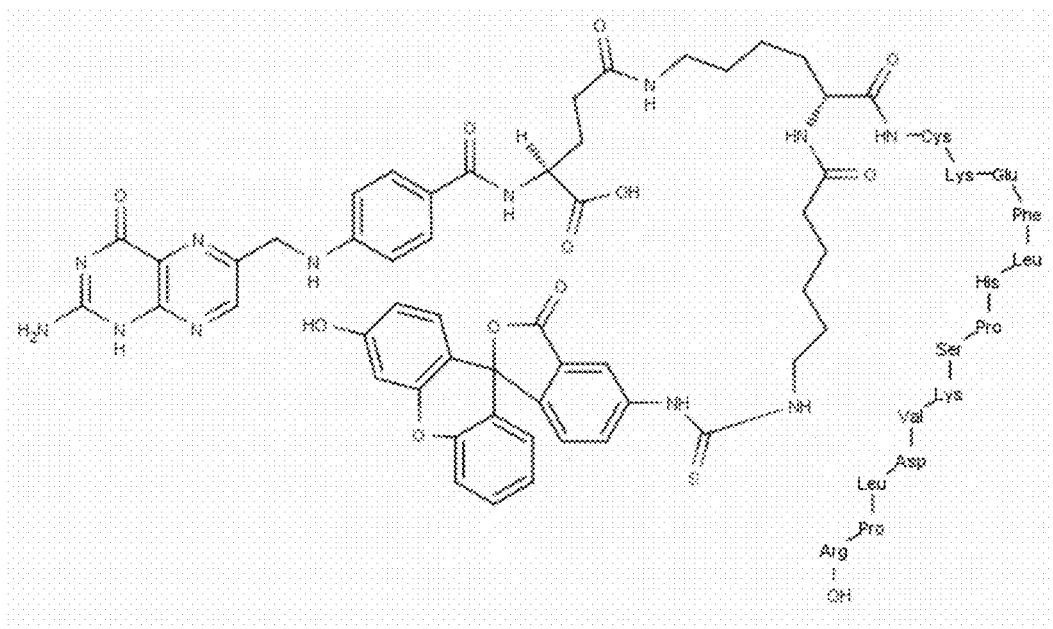

After deprotection and cleavage from resin, crude Folate-FITC was purified by HPLC to obtain product in yellow solid form with 95% purity. The structure of Folate-FITC was shown in FIG. 3.

Step VIII: Synthesis of 10A-FITC

P10 protected peptide resin 0.1 mmol (0.43 g) from Step II, was measured and added into a solid phase reaction column, DMF was then added, and followed by swelling with nitrogen gas bubbling for 30 mins. 2 eq. of Fmoc-e-ACP-OH, and then 2 eq. of DBLK was added to remove Fmoc protection group. The solution was washed with DMF for six times.

1.5 eq. of FITC in DMF was added to the resin, and followed by drop-wise addition of 3 eq. of DIEA. The reaction proceeded for 2 h and the resin was washed three times with DMF.

After deprotection and cleavage from resin, crude 10A-FITC was purified by HPLC to obtain 95% purity product yellow solid form. The structure of 10A-FITC was shown in FIG. 3.

Step IX: Synthesis of 10B-FITC

P10 protected peptide resin 0.1 mmol (0.43 g) from Step II, was measured and added into a solid phase reaction column, DMF was then added, and followed by swelling with nitrogen gas bubbling for 30 min. 2 eq. of Fmoc-Lys (Dde)-OH, Fmoc-e-ACP-OH, and then 2 eq. of DBLK was added to remove Fmoc protection group. The solution was washed with DMF for six times.

1.5 eq. of FITC in DMF was added to the resin, and followed by drop-wise addition of 3 eq. of DIEA. The reaction proceeded for 2 h and the resin was washed three times with DMF.

2% Hydrazine hydrate in DMF was added to the above resin and allowed to react for 15 min. Repeated twice then washed six times with DMF.

Folate-NHS (2 eq.) was measured and dissolved in DMSO, was added to the resin and reacted for 5 mins, DIEA (21 ml, 120 mmol) was added drop-wise, and the reaction was continued for 4 h at room temperature. The reaction product was washed with DMSO and DMF for three times, respectively, contracted with methanol, and dried in vacuo to obtain full protected peptide resin.

After deprotection and cleavage from resin, crude 10B-FITC was purified by HPLC to obtain 95% purity product yellow solid form. The structure of 10B-FITC was shown in FIG. 3.

Step X: Synthesis of LDC10B-CY5

P10 protected peptide resin 0.1 mmol (0.43 g) from Step II, was measured and added into a solid phase reaction column, DMF was then added, and followed by swelling with nitrogen gas bubbling for 30 mins. 2 eq. of Fmoc-Lys (Dde)-OH, and then 2 eq. of DBLK was added to remove Fmoc protection group. The solution was washed with DMF for six times.

100 mg of fluorescence dye Cy5, 1.5 eq HATU and 1.5 eq of HOBT in DMF was added to the resin, and followed by drop-wise addition of 3 eq. of DIEA. The reaction proceeded for 2 h and the resin was washed three times with DMF.

2% Hydrazine hydrate in DMF was added to the above resin and allowed to react for 15 min. Repeated twice then washed six times with DMF.

Folate-NHS (2 eq.) was measured and dissolved in DMSO, was added to the resin and reacted for 5 mins, DIEA (21 ml, 120 mmol) was added drop-wise, and the reaction was continued for 4 h at room temperature. The reaction product was washed with DMSO and DMF for three times, respectively, contracted with methanol, and dried in vacuo to obtain full protected peptide resin.

After deprotection and cleavage from resin, crude LDC10B-CY5 was purified by HPLC to obtain 95% purity product yellow solid form. LDC10B-CY5 is a fluorescence probe CY5 labeled version of LDC10B where the bi-ligand moiety is conjugated to CY5 dye through a lysine spacer.

Example II

Efficacy Assays of Conjugates

The involved conjugates are as follows: LDC10B, LDC10BX, LDC10BR, LDC11B, LDC12B, LDC13B, LDC1013, LDC10H, LDC11H, LDC13H, LDC1, LDC10A, LDC11A, and LDC13A. LDC1, LDC10A, LDC11A and LDC13A are used as controls in some experiments and their structures are as follows.

LDC1: Folate-(PEG)$_3$-MC-Val-Cit-PAB-MMAE
LDC10A: P10-MC-Val-Cit-PAB-MMAE
LDC11A: P11-MC-Val-Cit-PAB-MMAE
LDC13A: P13-MC-Val-Cit-PAB-MMAE 1. Endocytosis Test of Conjugate LDC10B The involved conjugates are as follows: Folate-FITC (FITC-ACP-Lys (Folate)-OH), 10B-FITC, and 10A-FITC.

Culture medium: RPMI 1640 Medium, no folic acid
Experimental methods:

1) human nasopharyngeal cancer cell line KB, melanoma cell line A375, human lung cancer cell H460, ovarian cancer cell SKOV3, breast cancer cell line HCC1954 were incubated at 37° C., 5% $CO_2$ in RPMI 1640 medium containing 10% fetal bovine serum, the cells were passaged every 2-3 days.

2) human nasopharyngeal cancer cell line KB, melanoma cell line A375, human lung cancer cell H460, ovarian cancer cell SKOV3, breast cancer cell line HCC1954 were plated at $1\times10^3$ cells per well (96-well plate) and incubated for 8-12 h at 37° C., 5% $CO_2$.

3) 1 µM of FITC conjugates or control was added to the cells in the plate and incubated for 10-15 min at 37° C. The culture medium in the wells was then removed by aspiration and the cells were washed with PBS for three times.

4) cells were then imaged with confocal microscope (brand) to visualize endocytosis.

Figure 2:
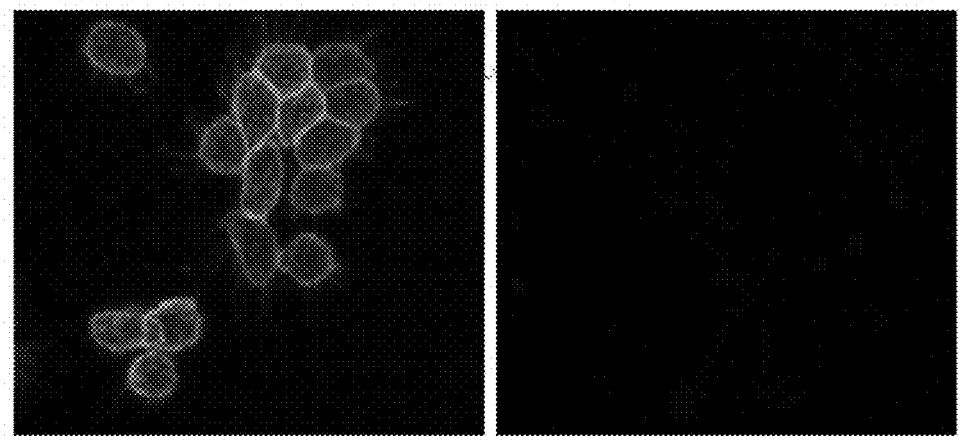
FIG. 2 shows the endocytosis test results of LDC10B. Panels A and B show that Folate-FITC enters KB cells (folate receptor positive cells) but not A375 cells (folate receptor negative cells); Panels C and D show that 10A-FITC cannot enter either KB cells or A375 cells; Panels E and F show that bi-ligand conjugate 10B-FITC enters KB cells but not A375 cells.
Figure 2:
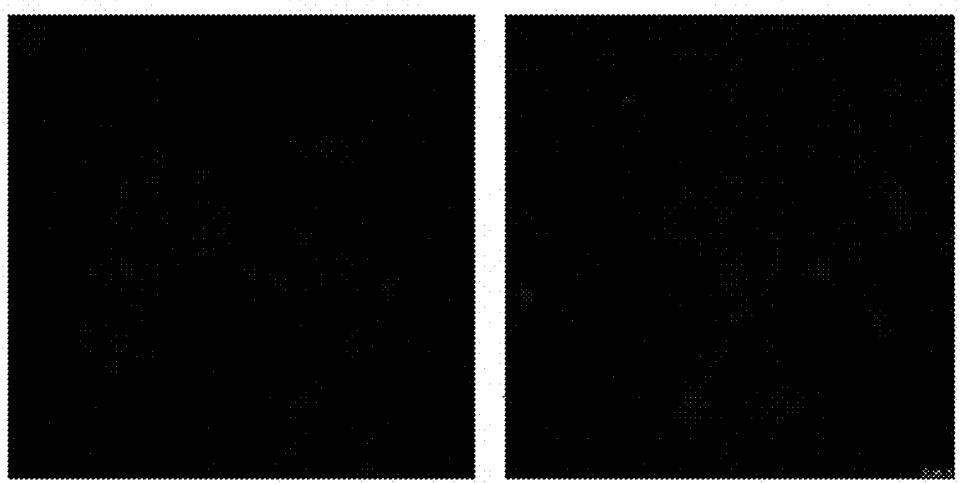
Figure 2:
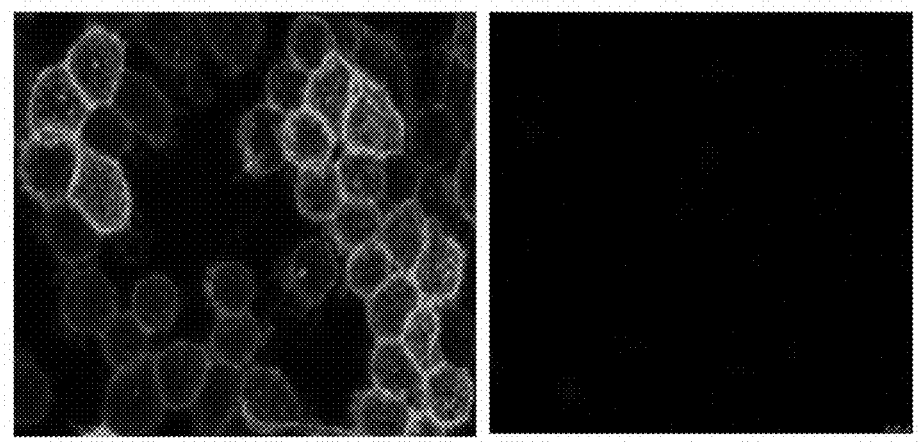

Results and Analysis:

To show that adding a folate ligand can confer folate Receptor mediated endocytosis to Bi-ligand LDC10B, KB (folate receptor positive cell) and A375 (folate receptor negative cell) were tested with 10A-FITC, Folate-FITC, and 10B-FITC. As shown in FIG. 2, Folate-FITC enters KB (Folate Receptor positive cell) but not A375 (Folate Receptor negative cell) (Panels A and B) through Folate Receptor mediated endocytosis, while 10A-FITC cannot enter either cell (Panels C and D) due to lack of endocytosis. However, adding Folate ligand converting 10A-FITC into a bi-ligand conjugate, i.e. 10B-FITC conferred the conjugate the ability to enter KB (Panel E) but not A375 (Panel F) through Folate Receptor mediated endocytosis. Furthermore, pre-incubating KB cells with 50 mM (50 fold excess of conjugate) free Folate completely blocked the endocytosis of both Folate-FITC and 10B-FITC (data not shown), confirming the endocytosis was indeed mediated by Folate Receptor.

2. Cytotoxicity Test of Conjugate LDC10B
Test sample: LDC10B
Control samples: MMAE, LDC1, LDC10A
Culture medium: RPMI 1640 Medium, no folic acid
Experimental methods:
1) human nasopharyngeal cancer cell line KB, melanoma cell line A375, human lung cancer cell H1299, chronic myeloid leukemia cell line K562, human lung cancer cell H460, ovarian cancer cell SKOV3, breast cancer cell line HCC1954, human gastric cancer cell N87, and human breast cancer cell SK-BR-3 were incubated at 37° C., 5% $CO_2$ in RPMI 1640 medium containing 10% fetal bovine serum, the cells were passaged every 2-3 days.
2) human nasopharyngeal cancer cell line KB, melanoma cell line A375, human lung cancer cell H1299, chronic myeloid leukemia cell line K562, human lung cancer cell H460, ovarian cancer cell SKOV3, breast cancer cell line HCC1954, human gastric cancer cell N87, and human breast cancer cell SK-BR-3 were plated at $1\times10^3$ cells per well (96-well plate) and incubated for 8-12 h at 37° C., 5% $CO_2$.
3) Stock solutions of LDC conjugates or controls were prepared in PBS solution. 100 μL/well of serially diluted LDC conjugates or controls was added to the test cells in the plates and incubated for 15-30 min at 37° C., 5% $CO_2$. The culture medium in the wells was then removed by aspiration and the test cells were incubated in fresh culture medium without conjugates (150 μL/well) for 2-3 days at 37° C., 5% $CO_2$.
4) CellTiter 96® Aqueous One Solution Cell Proliferation Assay (Promega) was added to each well to measure the amount of dead cells, and each plate was incubated in an incubator for 1 h at 37° C., 5% $CO_2$.
5) Each plate was read at 490 nm on a microplate reader, and the cell survivals were compared for test cells with or without the treatment of LDC conjugates. The LDC drug concentrations that are required for 50% cell death ($IC_{50}$ values) were determined.

Results and Analysis:
LDC10B can kill the following cancer cells very efficiently: human nasopharyngeal cancer cell line KB, human lung cancer cell H460, human lung cancer cell H1299, chronic myeloid leukemia cell line K562, ovarian cancer cell SKOV3, breast cancer cell line HCC1954, human gastric cancer cell N87, human breast cancer cell SK-BR-3, and the $IC_{50}$ values of LDC10B were lower (stronger) than those of LDC1 and LDC10A controls (see Table 4). These cell lines are known to have expression of Folate receptor and/or TRPV6 receptor. However, the cytotoxicity of LDC10B is significantly lower (higher IC50 readings) to the melanoma cell line A375 lacking Folate receptor expression.

LDC10B is a bi-ligand drug conjugate that can bind to both folate receptor and TRPV6 receptor. For receptor positive cell lines, It can be seen from Table 5 that the cytotoxicity of LDC10B was 2-15 times stronger ($IC_{50}$ value was 2-15 times less) than single-ligand drug conjugate LDC1 or LDC10A. For melanoma cell line A375 lacking Folate receptor, LDC10B, similar to LDC1 and LDC10A, is about 15 fold less toxic indicating good specificity. Therefore, bi-ligand drug conjugate LDC10B shows synergistic effects and contribute to the efficacy of drugs.

TABLE 4

Cytotoxicity Test Results ($IC_{50}$ values) of Conjugate LDC10B vs Controls (Unit: mol/l, M)

TABLE 4A: Incubation Time 30 min

| CELL | H1299 | K562 | H460 | SKOV3 | HCC1954 | N87 | SK-BR-3 |
|---|---|---|---|---|---|---|---|
| MMAE | $0.86 \times 10^{-9}$ | $0.54 \times 10^{-9}$ | $0.77 \times 10^{-9}$ | $0.62 \times 10^{-9}$ | $0.45 \times 10^{-9}$ | $0.68 \times 10^{-9}$ | $0.52 \times 10^{-9}$ |
| LDC1 | $2.62 \times 10^{-7}$ | $9.31 \times 10^{-8}$ | $1.92 \times 10^{-7}$ | $1.02 \times 10^{-7}$ | $9.44 \times 10^{-8}$ | $2.39 \times 10^{-7}$ | $9.82 \times 10^{-8}$ |
| LDC10A | $5.09 \times 10^{-7}$ | $1.11 \times 10^{-7}$ | $4.83 \times 10^{-7}$ | $1.25 \times 10^{-7}$ | $1.06 \times 10^{-7}$ | $5.17 \times 10^{-7}$ | $1.09 \times 10^{-7}$ |
| LDC10B | $5.88 \times 10^{-8}$ | $1.48 \times 10^{-8}$ | $5.04 \times 10^{-8}$ | $1.57 \times 10^{-8}$ | $1.41 \times 10^{-8}$ | $7.51 \times 10^{-8}$ | $1.59 \times 10^{-8}$ |

Table 4B: Incubation Time 15 min

| CELL | A375 | KB |
|---|---|---|
| MMAE | $1 \times 10^{-7}$ | $8.9 \times 10^{-8}$ |
| LDC1 | $1 \times 10^{-5}$ | $1.5 \times 10^{-5}$ |
| LDC10A | $1 \times 10^{-5}$ | $8.5 \times 10^{-6}$ |
| LDC10B | $1 \times 10^{-5}$ | $7.6 \times 10^{-7}$ |

3. Cytotoxicity Test of Conjugate LDC11B
Test sample: LDC11B
Control samples: MMAE, LDC1, LDC11A
Culture medium: RPMI 1640 Medium, no folic acid
Experimental methods:
1) human lung cancer cell H460, ovarian cancer cell SKOV3, human embryonic kidney cell 293A were incubated at 37° C., 5% $CO_2$ in RPMI 1640 medium containing 10% fetal bovine serum, the cells were passaged every 2-3 days.
2) human lung cancer cell H460, ovarian cancer cell SKOV3, human embryonic kidney cell 293A were plated at $1\times10^3$ cells per well (96-well plate) and incubated for 8-12 h at 37° C., 5% $CO_2$.
3) Stock solutions of LDC conjugates or control were prepared in PBS solution. 100 μL/well of serially diluted LDC conjugates or control was added to the cells in the plate and incubated for 15-30 min at 37° C., 5% $CO_2$. The culture medium in the wells was then removed by aspiration and the cells were incubated in fresh culture medium without conjugates (150 μL/well) for 2-3 days at 37° C., 5% $CO_2$.

4) CellTiter 96® Aqueous One Solution Cell Proliferation Assay (Promega) was added to each well to measure the amount of dead cells, and the plate was incubated in an incubator for 1 h at 37° C., 5% $CO_2$.

5) The plate was read at 490 nm on a microplate reader, and the cell survivals were compared for cells with or without the treatment of LDC conjugates. The LDC drug concentrations that are required for 50% cell death ($IC_{50}$ values) were determined.

Results and Analysis:

LDC11B can kill the following cancer cells or inhibit their growths: human lung cancer cell H460, ovarian cancer cell SKOV3, human embryonic kidney cell 293A. These cell lines are known to have high level expression of Folate receptor and/or LHRH receptor. The $IC_{50}$ values of LDC11B were lower than those of LDC1 and LDC11A controls (see Table 5).

LDC11B is a bi-ligand drug conjugate that can bind both folate receptor and LHRH receptor. It can be seen from Table 5 that the cytotoxicity of LDC11B was almost ten times stronger ($IC_{50}$ value was almost ten times less) than single-ligand conjugate LDC1 or LDC11A. Therefore, bi-ligand drug conjugate LDC11B shows synergistic effects and contribute to the efficacy of drugs.

TABLE 5

Cytotoxicity Test Results ($IC_{50}$ values) of Conjugate LDC11B vs Controls

| CELL | H460 | SKOV3 | (Unit: mol/l, M) 293A |
|---|---|---|---|
| MMAE | $0.58 \times 10^{-9}$ | $0.44 \times 10^{-9}$ | $0.86 \times 10^{-9}$ |
| LDC1 | $5.26 \times 10^{-7}$ | $2.95 \times 10^{-7}$ | $7.15 \times 10^{-7}$ |
| LDC11A | $6.67 \times 10^{-7}$ | $3.41 \times 10^{-7}$ | $1.31 \times 10^{-6}$ |
| LDC11B | $8.13 \times 10^{-8}$ | $4.38 \times 10^{-8}$ | $5.24 \times 10^{-7}$ |

4. Cytotoxicity Test of Conjugate LDC12B

Test sample: LDC12B

Control sample: MMAE

Culture medium: RPMI 1640 Medium, no folic acid

Experimental methods:

1) human endometrial cancer cell HEC-1A, human gastric cancer cell line GTL-16, human colon carcinoma HCT-116, human neuroblastoma cell line SH-SY5Y were incubated at 37° C., 5% $CO_2$ in RPMI 1640 medium containing 10% fetal bovine serum, the cells were passaged every 2-3 days.

2) human endometrial cancer cell HEC-1A, human gastric cancer cell line GTL-16, Human colon carcinoma HCT-116, human neuroblastoma cell line SH-SY5Y were plated at $1 \times 10^3$ cells per well (96-well plate) and incubated for 8-12 h at 37° C., 5% $CO_2$.

3) Stock solutions of LDC conjugates or control were prepared in PBS solution. 100 µL/well of serially diluted LDC conjugates or control was added to the cells in the plate and incubated for 15-30 min at 37° C., 5% $CO_2$. The culture medium in the wells was then removed by aspiration and the cells were incubated in fresh culture medium without conjugates (150 µL/well) for 2-3 days at 37° C., 5% $CO_2$.

4) CellTiter 96® Aqueous One Solution Cell Proliferation Assay (Promega) was added to each well to measure the amount of dead cells, and the plate was incubated in an incubator for 1 h at 37° C., 5% $CO_2$.

5) the plate was read at 490 nm on a microplate reader, and the cell survivals were compared for cells with or without the treatment of LDC conjugates. The LDC drug concentrations that are required for 50% cell death ($IC_{50}$ values) were determined.

Results and Analysis:

LDC12B can kill the following cancer cells or inhibiting their growths: human endometrial cancer cell HEC-1A, human gastric cancer cell line GTL-16, Human colon carcinoma HCT-116, human neuroblastoma cell line SH-SY5Y. The $IC_{50}$ values were shown in Table 6.

TABLE 6

Cytotoxicity Test Results ($IC_{50}$ values) of Conjugate LDC12B vs MMAE

| CELL | HCT-116 | GTL-16 | HEC-1A | (Unit: mol/l, M) SH-SY5Y |
|---|---|---|---|---|
| MMAE | $1.27 \times 10^{-8}$ | $6.38 \times 10^{-9}$ | $8.74 \times 10^{-9}$ | $2.4 \times 10^{-8}$ |
| LDC12B | $8.26 \times 10^{-7}$ | $6.12 \times 10^{-7}$ | $6.31 \times 10^{-7}$ | $3.96 \times 10^{-7}$ |

5. Cytotoxicity Test of Conjugate LDC13B

Test sample: LDC13B

Control samples: MMAE, LDC1, LDC13A

Culture medium: RPMI 1640 Medium, no folic acid

Experimental methods:

1) human nasopharyngeal cancer cell line KB, human colon carcinoma HCT-116, human prostatic cancer cell PC-3, human gastric cancer cell line GTL-16, human endometrial cancer cell HEC-1A, and human gastric cancer cell N87 were incubated at 37° C., 5% $CO_2$ in RPMI 1640 medium containing 10% fetal bovine serum, the cells were passaged every 2-3 days.

2) human nasopharyngeal cancer cell line KB, human colon carcinoma HCT-116, human prostatic cancer cell PC-3, human gastric cancer cell line GTL-16, human endometrial cancer cell HEC-1A, and human gastric cancer cell N87 were plated at $1 \times 10^3$ cells per well (96-well plate) and incubated for 8-12 h at 37° C., 5% $CO_2$.

3) Stock solutions of LDC conjugates or control were prepared in PBS solution. 100 µL/well of serially diluted LDC conjugates or control was added to the cells in the plate and incubated for 15-30 min at 37° C., 5% $CO_2$. The culture medium in the wells was then removed by aspiration and the cells were incubated in fresh culture medium without conjugates (150 µL/well) for 2-3 days at 37° C., 5% $CO_2$.

4) CellTiter 96® Aqueous One Solution Cell Proliferation Assay (Promega) was added to each well to measure the amount of dead cells, and the plate was incubated in an incubator for 1 h at 37° C., 5% $CO_2$.

5) the plate was read at 490 nm on a microplate reader, and the cell survivals were compared for cells with or without the treatment of LDC conjugates. The LDC drug concentrations that are required for 50% cell death ($IC_{50}$ values) were determined.

Results and Analysis:

LDC13B can kill the following cancer cells or inhibit their growths: human nasopharyngeal cancer cell line KB, human colon cancer cell HCT-116, human gastric cancer cell line GTL-16, human endometrial cancer cell HEC-1A, human prostatic cancer cell PC-3, human gastric cancer N87. In particular, LDC13B is highly potent towards KB, which is a cell line with both folate and LHRH receptors. Furthermore, the bi-ligand LDC13B is 2-10 fold more potent than either of the single-ligand drug conjugates, i.e. LDC1 and LDC13A, confirming the advantage of bi-ligand drug conjugate in efficacy. The $IC_{50}$ values were shown in Table 7.

TABLE 7

Cytotoxicity Test Results (IC$_{50}$ values) of Conjugate LDC13B vs Controls

| CELL | KB | HCT-116 | GTL-16 | HEC-1A | PC-3 | (Unit: mol/l, M) N87 |
|---|---|---|---|---|---|---|
| MMAE | $2.88 \times 10^{-8}$ | $1.27 \times 10^{-8}$ | $6.38 \times 10^{-9}$ | $8.74 \times 10^{-9}$ | $1.28 \times 10^{-8}$ | $3.83 \times 10^{-9}$ |
| LDC1 | $6.5 \times 10^{-8}$ | — | — | — | — | — |
| LDC13A | $4.5 \times 10^{-6}$ | — | — | — | — | — |
| LDC13B | $2.57 \times 10^{-8}$ | $1.07 \times 10^{-6}$ | $7.55 \times 10^{-7}$ | $9.4 \times 10^{-7}$ | $1.18 \times 10^{-6}$ | $3.26 \times 10^{-7}$ |

6. Cytotoxicity Test of Conjugate LDC10H

Test sample: LDC10H
Control samples: MMAE, LDC1, LDC10A
Culture medium: RPMI 1640 Medium, no folic acid
Experimental methods:

1) human lung cancer cell H1299, ovarian cancer cell SKOV3, breast cancer cell line HCC1954, and human lung cancer cell H460 were incubated at 37° C., 5% CO$_2$ in RPMI 1640 medium containing 10% fetal bovine serum, the cells were passaged every 2-3 days.

2) human lung cancer cell H1299, ovarian cancer cell SKOV3, breast cancer cell line HCC1954, and human lung cancer cell H460 were plated at 1×10$^3$ cells per well (96-well plate) and incubated for 8-12 h at 37° C., 5% CO$_2$.

3) Stock solutions of LDC conjugates or control were prepared in PBS solution. 100 μL/well of serially diluted LDC conjugates or control was added to the cells in the plate and incubated for 15-30 min at 37° C., 5% CO$_2$. The culture medium in the wells was then removed by aspiration and the cells were incubated in fresh culture medium without conjugates (150 μL/well) for 2-3 days at 37° C., 5% CO$_2$.

4) CellTiter 96® Aqueous One Solution Cell Proliferation Assay (Promega) was added to each well to measure the amount of dead cells, and the plate was incubated in an incubator for 1 h at 37° C., 5% CO$_2$.

5) the plate was read at 490 nm on a microplate reader, and the cell survivals were compared for cells with or without the treatment of LDC conjugates. The LDC drug concentrations that are required for 50% cell death (IC$_{50}$ values) were determined.

Results and Analysis:

LDC10H can kill the following cells or inhibit their growths human lung cancer cell H1299, ovarian cancer cell SKOV3, breast cancer cell line HCC1954, and human lung cancer cell H460. The bi-ligand LDC10H is 10 fold more potent than mono-ligand drug conjugate LDC10A, indicating the membrane penetrating peptide sequence (H) is able to help with delivery of the drug into cells by endocytosis. Furthermore, LDC10H is also more potent than single-ligand conjugate LDC1, confirming the advantage of bi-ligand drug conjugate in efficacy. The IC$_{50}$ values of LDC10H were lower than LDC1 and LDC10A controls (see Table 8).

TABLE 8

Cytotoxicity Test Results (IC$_{50}$ values) of Conjugate LDC10H vs Controls

| CELL | HCC1954 | H1299 | SKOV3 | (Unit: mol/l, M) H460 |
|---|---|---|---|---|
| MMAE | $0.29 \times 10^{-9}$ | $0.71 \times 10^{-9}$ | $0.49 \times 10^{-9}$ | $0.56 \times 10^{-9}$ |
| LDC1 | $7.79 \times 10^{-8}$ | $1.86 \times 10^{-7}$ | $2.01 \times 10^{-7}$ | $1.37 \times 10^{-7}$ |
| LDC10A | $4.18 \times 10^{-7}$ | $7.88 \times 10^{-7}$ | $6.41 \times 10^{-7}$ | $7.24 \times 10^{-7}$ |
| LDC10H | $3.6 \times 10^{-8}$ | $9.04 \times 10^{-8}$ | $7.38 \times 10^{-8}$ | $8.53 \times 10^{-8}$ |

7. Cytotoxicity Test of Conjugate LDC1013
Control samples: MMAE, LDC1, LDC10A
Culture medium: RPMI 1640 Medium, no folic acid Experimental methods:

1) human nasopharyngeal cancer cell line KB, melanoma cell line A375, and human lung cancer cell H460 were incubated at 37° C., 5% CO$_2$ in RPMI 1640 medium containing 10% fetal bovine serum, the cells were passaged every 2-3 days.

2) human nasopharyngeal cancer cell line KB, melanoma cell line A375, and human lung cancer cell H460 were plated at 1×10$^3$ cells per well (96-well plate) and incubated for 8-12 h at 37° C., 5% CO$_2$.

3) Stock solutions of LDC conjugates or control were prepared in PBS solution. 100 μL/well of serially diluted LDC conjugates or control was added to the cells in the plate and incubated for 15-30 min at 37° C., 5% CO$_2$. The culture medium in the wells was then removed by aspiration and the cells were incubated in fresh culture medium without conjugates (150 μL/well) for 2-3 days at 37° C., 5% CO$_2$.

4) CellTiter 96® Aqueous One Solution Cell Proliferation Assay (Promega) was added to each well to measure the amount of dead cells, and the plate was incubated in an incubator for 1 h at 37° C., 5% CO$_2$.

5) the plate was read at 490 nm on a microplate reader, and the cell survivals were compared for cells with or without the treatment of LDC conjugates. The LDC drug concentrations that are required for 50% cell death (IC$_{50}$ values) were determined.

Results and Analysis:

LDC1013 is effective at killing the following cell lines human nasopharyngeal cancer cell line KB, human lung cancer cell H460, and inhibiting the growth of melanoma cell line A375 and the IC$_{50}$ values of LDC1013 were lower (Stronger) than those of LDC1 and LDC10A controls (see Table 9). However, the cytotoxicity of LDC1013 is significantly lower (higher IC50 readings) towards control cell line melanoma cell line A375.

LDC1013 is a bi-ligand drug conjugate that can bind to both LHRH receptor and TRPV6 receptor. For receptor positive cell lines, It can be seen from Table 9 that the cytotoxicity of LDC1013 was 2-15 times stronger (IC$_{50}$ value was 2-15 times less) than single-ligand drug conjugate LDC1 or LDC10A. For A375, LDC 1013 is about 10-100 fold less toxic than for H460 and KB, respectively, indicating good specificity. Therefore, bi-ligand drug conjugate LDC1013 shows synergistic effects and contribute to the efficacy of drugs.

TABLE 9

Cytotoxicity Test Results (IC$_{50}$ values) of Conjugate LDC1013 vs Controls

| | MMAE | FA-MMAE | LDC10A | (Unit: mol/l, M) LDC1013 |
|---|---|---|---|---|
| KB | $2 * 10^{-8}$ | $4 * 10^{-6}$ | $5.8 * 10^{-6}$M | $1.3 * 10^{-7}$ |
| H460 | $3.7 * 10^{-8}$ | $9.4 * 10^{-6}$ | $1.39 * 10^{-5}$M | $2.2 * 10^{-6}$ |
| A375 | $8.5 * 10^{-8}$ | $3.7 * 10^{-5}$ | $3.94 * 10^{-5}$M | $1.19 * 10^{-5}$ |

8. Cytotoxicity Test of Conjugate LDC10BR

Control samples: MMAE and LDC10B

Culture medium: RPMI 1640 Medium, no folic acid

Experimental methods:

1) human nasopharyngeal cancer cell line KB, melanoma cell line A375, and human lung cancer cell H460 were incubated at 37° C., 5% $CO_2$ in RPMI 1640 medium containing 10% fetal bovine serum, the cells were passaged every 2-3 days.

2) human nasopharyngeal cancer cell line KB, melanoma cell line A375, and human lung cancer cell H460 were plated at $1\times10^3$ cells per well (96-well plate) and incubated for 8-12 h at 37° C., 5% $CO_2$.

3) Stock solutions of LDC conjugates or control were prepared in PBS solution. 100 μL/well of serially diluted LDC conjugates or control was added to the cells in the plate and incubated for 15-30 min at 37° C., 5% $CO_2$. The culture medium in the wells was then removed by aspiration and the cells were incubated in fresh culture medium without conjugates (150 μL/well) for 2-3 days at 37° C., 5% $CO_2$.

4) CellTiter 96® Aqueous One Solution Cell Proliferation Assay (Promega) was added to each well to measure the amount of dead cells, and the plate was incubated in an incubator for 1 h at 37° C., 5% $CO_2$.

5) the plate was read at 490 nm on a microplate reader, and the cell survivals were compared for cells with or without the treatment of LDC conjugates. The LDC drug concentrations that are required for 50% cell death ($IC_{50}$ values) were determined.

Results and Analysis:

LDC10BR is effective at killing the following cell lines human nasopharyngeal cancer cell line KB, human lung cancer cell H460, and inhibiting the growth of melanoma cell line A375 and the $IC_{50}$ values of LDC10BR were comparable to the bi-ligand conjugate LDC10B (see Table 10).

LDC10BR is a tri-ligand drug conjugate that can bind to RGD (Integrin alpha) receptor, Folate receptor, and TRPV6 receptor. For receptor positive cell lines, it can be seen from Table 10 that the cytotoxicity of LDC10BR was comparable to the bi-ligand conjugate LDC10B. Therefore, tri-ligand drug conjugate LDC10BR is at least as effective as bi-ligand LDC10B. Furthermore, a tri-ligand LDC may have superior cytotoxicity and selectivity towards cancer cells with expression of all three receptors with the three ligands showing synergistic effects and contribute to the efficacy of drugs.

TABLE 10

Cytotoxicity Test Results ($IC_{50}$ values) of Conjugate LDC10BR vs LDC10B

|  | MMAE | LDC10B | (Unit: mol/l, M) LDC10BR |
|---|---|---|---|
| KB | $2 * 10^{-8}$ | $2.2 * 10^{-6}$ | $6.6 * 10^{-6}$ |
| H460 | $3.7 * 10^{-8}$ | $6.8 * 10^{-6}$ | $6.4 * 10^{-6}$ |
| A375 | $8.5 * 10^{-8}$ | $5.13 * 10^{-5}$ | $3.81 * 10^{-5}$ |

Example III

Efficacy Study of Conjugates in Animal Models

Objective: to explore the anti-tumor efficacy of conjugates in mice models for the treatment of cancers.

1. Inhibitory Assay of Conjugates LDC10B and LDC10H Against Xenograf Tumors

Conjugates used for treatment: LDC10B, LDC10H

Animal: nude mice, aged 6-8 weeks, female

Experimental methods:

1) human large cell lung cancer cell H460, human lung cancer cell A549, ovarian cancer cell SKOV3, and breast cancer cell line HCC1954 were incubated at 37° C., 5% $CO_2$ in IMDM medium containing 10% fetal bovine serum, the cells were passaged every 2-3 days.

2) generation of tumors: $7\times10^6$ tumor cells were injected subcutaneously into the back of nude mice, and the mice were grouped for treatment after the tumor sizes were as large as about 100-200 $mm^3$.

3) treatment: 3 mice/group, treated with LDC10B, LDC10H, as well as controls MMAE and PBS with doses of 5 and 10 mg/kg every 5 days, three injections.

4) the physical performance, body weights and tumor sizes of the animals were monitored. The number of animal death was recorded during the experiment.

Results and Analysis:

LDC10B and LDC10H can inhibit the tumor growth of human large cell lung cancer cell H460, ovarian cancer cell SKOV3, and breast cancer cell line HCC1954, most tumors disappeared after three injections at doses of 5 and 10 mg/kg. The detailed results were shown in Table 11 and Table 12.

TABLE 11

Inhibitory Efficacy of Conjugate LDC10B against Xenograf Tumors

|  | Transplanted H460 tumor | | | | Transplanted HCC1954 tumor | | Transplanted SKOV3 tumor | |
|---|---|---|---|---|---|---|---|---|
|  | 5 mg/kg | | 10 mg/kg | | 10 mg/kg | | 10 mg/kg | |
| Time | Body weight of mice (g) | Tumor size ($mm^3$) | Body weight of mice (g) | Tumor size ($mm^3$) | Body weight of mice (g) | Tumor size ($mm^3$) | Body weight of mice (g) | Tumor size ($mm^3$) |
| Before Injection | 23.13 | 89.25 | 22.51 | 97.38 | 21.85 | 225.32 | 22.96 | 178.68 |
| Five days after Injection 1 | 22.53 | 78.63 | 22.53 | 45.74 | 22.2 | 108.73 | 22.44 | 163.05 |
| Five days after Injection 2 | 22.26 | 49.11 | 23.37 | 6.32 | 22.55 | 0 | 23.23 | 120.51 |

TABLE 11-continued

Inhibitory Efficacy of Conjugate LDC10B against Xenograf Tumors

| | Transplanted H460 tumor | | | | Transplanted HCC1954 tumor | | Transplanted SKOV3 tumor | |
| --- | --- | --- | --- | --- | --- | --- | --- | --- |
| | 5 mg/kg | | 10 mg/kg | | 10 mg/kg | | 10 mg/kg | |
| Time | Body weight of mice (g) | Tumor size ($mm^3$) | Body weight of mice (g) | Tumor size ($mm^3$) | Body weight of mice (g) | Tumor size ($mm^3$) | Body weight of mice (g) | Tumor size ($mm^3$) |
| Five days after Injection 3 | 21.65 | 52.5 | 23 | 0 | 22.38 | 0 | 23.53 | 68.31 |

TABLE 12

Inhibitory Efficacy of Conjugate LDC10H against Xenograf Tumors

| | Transplanted H460 Tumor | | | | Transplanted HCC1954 Tumor | |
| --- | --- | --- | --- | --- | --- | --- |
| | 5 mg/kg | | 10 mg/kg | | 10 mg/kg | |
| LDC10H | Body weight of mice (g) | Tumor size ($mm^3$) | Body weight of mice (g) | Tumor size ($mm^3$) | Body weight of mice (g) | Tumor size ($mm^3$) |
| Before Injection | 23.29 | 136.49 | 23.37 | 126 | 22.05 | 88.6 |
| Five days after Injection 1 | 24.26 | 71.51 | 24.39 | 108.15 | 23.32 | 16.77 |
| Five days after Injection 2 | 23.14 | 65.73 | 22.12 | 37.5 | 22.87 | 0 |
| Five days after Injection 3 | 23.22 | 11.64 | 23.61 | 2.34 | 22.51 | 0 |

2. Inhibitory Assay of Conjugates LDC11A, LDC11B Against Xenograf Tumors

Conjugates used for treatment: LDC11A and LDC11B
Animal: nude mice, aged 6-8 weeks, female
Experimental methods:

1) human large cell lung cancer cell H460, ovarian cancer cell SKOV3, breast cancer cell line HCC1954, and human breast cancer cell SK-BR-3 were incubated at 37° C., 5% $CO_2$ in IMDM medium containing 10% fetal bovine serum, the cells were passaged every 2-3 days.

2) generation of tumors: $7 \times 10^6$ tumor cells were subcutaneously injected into the back of nude mice, and the mice were grouped for treatment after the tumor sizes were as large as about 100~200 $mm^3$.

3) treatment: 3 mice/group, treated with LDC11A, LDC11B, as well as controls MMAE and PBS with doses of 5 and 10 mg/kg every 5 days, three injections.

4) the physical performance, body weights and tumor sizes of the animals were monitored. The number of animal death was recorded during the experiment.

Results and Analysis:

LDC11B can inhibit the tumor growth of human large cell lung cancer cell H460, ovarian cancer cell SKOV3, and breast cancer cell line HCC1954, most tumors were disappeared after continuous three injections at the dose of 10 mg/kg. While with respect to LDC11A, the animals were dead after the first injection due to the strong toxicity. The detailed results were shown in Table 13 and Table 14.

TABLE 13

Inhibitory Efficacy of Conjugate LDC11B against Xenograf Tumors

| | Transplanted H460 tumor | | Transplanted SKOV3 tumor | | Transplanted HCC1954 tumor | |
| --- | --- | --- | --- | --- | --- | --- |
| | 10 mg/kg | | 10 mg/kg | | 10 mg/kg | |
| Time | Body weight of mice (g) | Tumor size ($mm^3$) | Body weight of mice (g) | Tumor size ($mm^3$) | Body weight of mice (g) | Tumor size ($mm^3$) |
| Before Injection | 21.85 | 225.32 | 22.11 | 169.22 | 22.76 | 218.76 |
| Five days after Injection 1 | 22.2 | 108.73 | 24.28 | 137.66 | 22.56 | 87.51 |
| Five days after Injection 2 | 22.55 | 0 | 23.6 | 76.13 | 23.15 | 0 |

TABLE 13-continued

Inhibitory Efficacy of Conjugate LDC11B against Xenograf Tumors

| Time | Transplanted H460 tumor 10 mg/kg | | Transplanted SKOV3 tumor 10 mg/kg | | Transplanted HCC1954 tumor 10 mg/kg | |
|---|---|---|---|---|---|---|
| | Body weight of mice (g) | Tumor size (mm$^3$) | Body weight of mice (g) | Tumor size (mm$^3$) | Body weight of mice (g) | Tumor size (mm$^3$) |
| Five days after Injection 3 | 22.38 | 0 | 24.92 | 27.84 | 23.48 | 0 |

TABLE 14

Inhibitory Efficacy of Conjugate LDC11A against Xenograf Tumors

| LDC11A | Transplanted H460 Tumor 10 mg/kg | |
|---|---|---|
| | Body weight of mice (g) | Tumor size (mm$^3$) |
| Before Injection | 24.46 | 294 |
| Three days after Injection 1 | 18.25 | 300 |
| Five days after Injection 1 | Death | Death |

3. Inhibitory Assay of Conjugates LDC13B Against Xenograf Tumors

Conjugates used for treatment: LDC13B
Animal: nude mice, aged 6-8 weeks, female
Experimental methods:
1) human large cell lung cancer cell H460 were incubated at 37° C., 5% CO$_2$ in IMDM medium containing 10% fetal bovine serum, the cells were passaged every 2-3 days.
2) generation of tumors: 7×10$^6$ tumor cells were injected subcutaneously into the back of nude mice, and the mice were grouped for treatment after the tumor sizes were as large as about 200 mm$^3$.
3) treatment: 3 mice/group, treated with LDC13B as well as controls MMAE and PBS with doses of 2.5 and 5 mg/kg every 3 days, four injections.
4) the physical performance, body weights and tumor sizes of the animals were monitored. The number of animal death was recorded during the experiment.
Results and Analysis:
LDC13B can inhibit the tumor growth of human large cell lung cancer cell H460, most tumors shrank rapidly at 2.5 mg/kg dose and completely disappeared after four injections at doses of 5 mg/kg. The detailed results were shown in Table 15.

TABLE 15

Inhibitory Efficacy of Conjugate LDC13B against Xenograf Tumor

| | Transplanted H460 tumor | | | |
|---|---|---|---|---|
| | 2.5 mg/kg | | 5 mg/kg | |
| Time | Body weight of mice (g) | Tumor size (mm$^3$) | Body weight of mice (g) | Tumor size (mm$^3$) |
| Before Injection | 22.7 | 294 | 20.95 | 196 |
| 3 days after Injection 1 | 22.73 | 384 | 18.36 | 144 |
| 3 days after Injection 2 | 22.65 | 384 | 19.65 | 40 |
| 3 days after Injection 3 | 22.47 | 144 | 18.21 | 18 |
| 3 days after Injection 4 | 21.76 | 144 | 18.22 | 13.5 |

4. Inhibitory Assay of Conjugates LDC1013 Against Xenograf Tumors

Conjugates used for treatment: LDC1013
Animal: nude mice, aged 6-8 weeks, female
Experimental methods:
1) Human breast cancer cells HCC1954 were incubated at 37° C., 5% CO$_2$ in IMDM medium containing 10% fetal bovine serum, the cells were passaged every 2-3 days.
2) generation of tumors: 7×10$^6$ tumor cells were injected subcutaneously into the back of nude mice, and the mice were grouped for treatment after the tumor sizes were as large as about 180-320 mm$^3$.
3) treatment: 3 mice/group, treated with LDC1013 as well as controls MMAE and PBS with doses of 2.5 and 5 mg/kg every 3 days, four injections.
4) the physical performance, body weights and tumor sizes of the animals were monitored. The number of animal death was recorded during the experiment.
Results and Analysis:
LDC1013 can completely eliminate HCC1954 xenograf tumor, after 7 doses at 2.5 mg/kg and 7 doses of 5 mg/kg injected every three days, respectively. The detailed results were shown in Table 16.

TABLE 16

Inhibitory Efficacy of Conjugate LDC1013 against Xenograf Tumor

| | Transplanted HCC1954 tumor | | | |
|---|---|---|---|---|
| | 2.5 mg/kg | | 5 mg/kg | |
| Time | Body weight of mice (g) | Tumor size (mm$^3$) | Body weight of mice (g) | Tumor size (mm$^3$) |
| Before Injection | 24.14 | 180 | 21.92 | 320 |
| 3 days after Injection 1 | 24.46 | 198 | 20.7 | 405 |
| 3 days after Injection 2 | 24.54 | 198 | 20.43 | 405 |
| 3 days after Injection 3 | 23.94 | 180 | 21.31 | 288 |
| 3 days after Injection 4 | 24.3 | 113 | 21.15 | 88 |

TABLE 16-continued

Inhibitory Efficacy of Conjugate LDC1013 against Xenograf Tumor

| | Transplanted HCC1954 tumor | | | |
|---|---|---|---|---|
| | 2.5 mg/kg | | 5 mg/kg | |
| Time | Body weight of mice (g) | Tumor size (mm³) | Body weight of mice (g) | Tumor size (mm³) |
| 4 days after Injection 5 | 24.98 | 64 | 21.21 | 40 |
| 5 days after Injection 6 | 24.73 | 22 | 20.49 | 0 |
| 6 days after Injection 7 | 24.43 | 0 | 24.49 | — |

5. Inhibitory Assay of Conjugates LDC10BX Against Xenograf Tumors

Conjugates used for treatment: LDC10BX
Animal: nude mice, aged 6-8 weeks, female
Experimental methods:

1) Human lung cancer cell H460 were incubated at 37° C., 5% $CO_2$ in IMDM medium containing 10% fetal bovine serum, the cells were passaged every 2-3 days.

2) generation of tumors: $7 \times 10^6$ tumor cells were injected subcutaneously into the back of nude mice, and the mice were grouped for treatment after the tumor sizes were as large as about 180-320 mm³.

3) treatment: 3 mice/group, treated with LDC10BX as well as control LDC13A with a dose of 10 mg/kg every 3 days, three injections.

4) the physical performance, body weights and tumor sizes of the animals were monitored. The number of animal death was recorded during the experiment.

Results and Analysis:

LDC10BX eliminated H460 xenograf tumor, after 3 doses at 10 mg/kg injected every three days.

6. Detection of Conjugate Concentrations in Xenograf Tumor Models

Samples: LDC10B, LDC10H
Animal: nude mice, aged 6-8 weeks, female
Experimental methods:

1) Human ovarian cancer cell SKOV3 and breast cancer cell line HCC1954 were incubated at 37° C., 5% $CO_2$ in IMDM medium containing 10% fetal bovine serum, the cells were passaged every 2-3 days.

2) generation of tumors: $7 \times 10^6$ tumor cells were injected subcutaneously into the back of nude mice, and the mice were grouped for treatment after the tumor sizes were as large as about 100~200 mm³.

3) treatment: 3 mice/group, 10 mg/kg, peritoneal injection.

4) blood collection: the time for blood collection before treatment was set as 0, blood was collected at 20 min, 2 h, 4 h, and 24 h after treatment. The blood was centrifuged to collect serum, which was frozen and preserved.

5) Detection: the total amount of MMAE, LDC10B, LDC10H, as well as the MMAE metabolites of LDC10B and LDC10H in serum were detected by mice anti-MMAE ELISA kit.

Results and Analysis:

Trace amount of LDC10B were detected in serum at 24 h after treatment, while none of LDC10H and its MMAE metabolite was detected, indicating that free drugs were excreted/metabolized fast in vivo. The detailed results are as shown in Table 17.

TABLE 17

Concentrations of Conjugates in Animals with Xenograf Tumors

| Concentration (ug/ml) | LDC10B | LDC10H |
|---|---|---|
| Before Treatment | 0 | 0 |
| 20 min | 10.8 | 0.77 |
| 2 h | 5.035 | 0.58 |
| 4 h | 0.53 | 0.196 |
| 24 h | 0.1179 | 0 |

In light of the above, the studies in vitro and in vivo have shown that:

(a) multiple-Ligand drug conjugates (mLDCs) bind to target cells and/or enter target cells by endocytosis and kill the cells through the effect of cytotoxic payload. Over 20 different cancer cell lines have been tested and the results confirmed the above conclusion.

Figure 4:
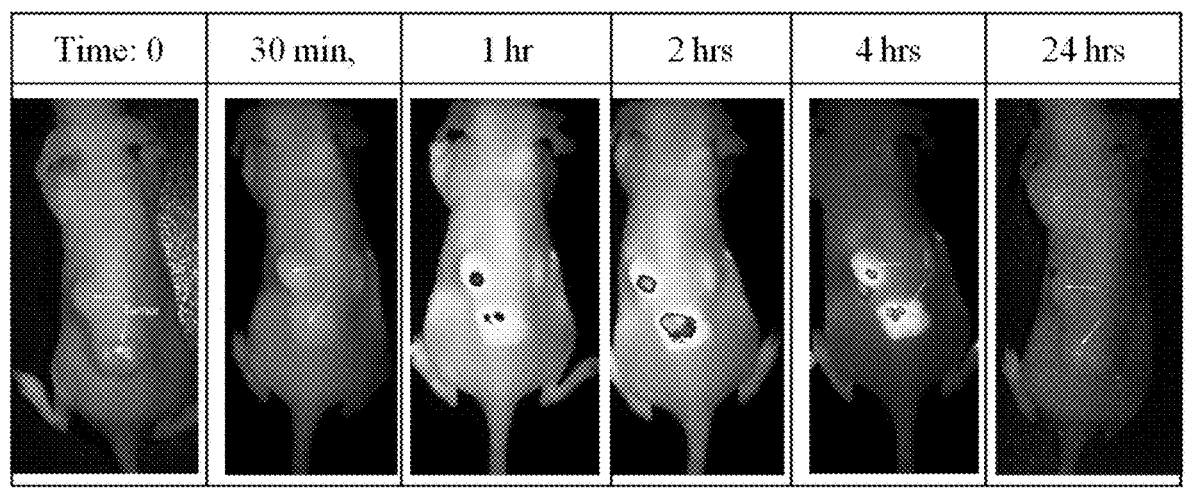
FIG. 4 shows live mouse imaging showing fluorescence-labeled LDC10B-Cy5 concentrating on tumor site.

(b) in vivo live animal imaging showed that fluorescence labeled LDC10B-Cy5 concentrates in situ of tumor mass and last over 24 hrs (see FIG. 4).

(c) mLDCs can completely eliminate xenograf tumor in mice models. Most of the lead compounds showed excellent efficacy controlling or eliminating xenograf tumors in a dose and receptor expression level dependent fashion without causing weight loss or other obvious toxicity. When tumors were total eliminated, mice remained tumor free for the rest of their lives (>6 months).

What is claimed is:

1. A conjugate compound or a pharmaceutically acceptable salt thereof, comprising a payload; and a plurality of cell-interacting molecules comprising first and second cell-interacting molecules, wherein
the first cell-interacting molecule comprises a first ligand, and
the second cell-interacting molecule comprises
an endocytosis molecule capable of mediating endocytosis,
wherein the first ligand comprises a peptide having the amino acid sequence SEQ ID NO: 15 which is capable of specifically binding to a transient receptor potential cation channel subfamily V member 6 (TRPV6),
wherein the endocytosis molecule is selected from the group consisting of folate and analogs thereof,
wherein the payload is selected from the group consisting of a small molecule compound, a nucleotide, a peptide, and a protein, wherein the payload is conjugated with at least one of the cell-interacting molecules directly or via a linker.

2. The conjugate compound of claim 1, or a pharmaceutically acceptable salt thereof, wherein the payload is conjugated with at least one of the cell-interacting molecules via a linker.

3. The conjugate compound of claim 1, or a pharmaceutically acceptable salt thereof, wherein the payload is a small molecule compound that is auristatins or any derivatives thereof.

4. A conjugate compound, or a pharmaceutically acceptable salt thereof, wherein the conjugate compound is selected from the group consisting of the following compounds:

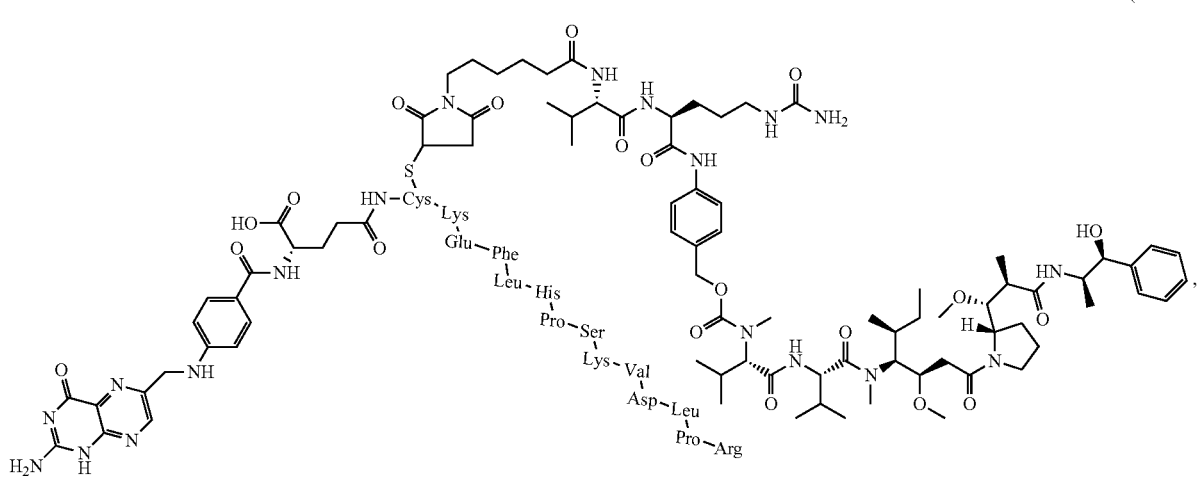

(LDC10B)

-continued
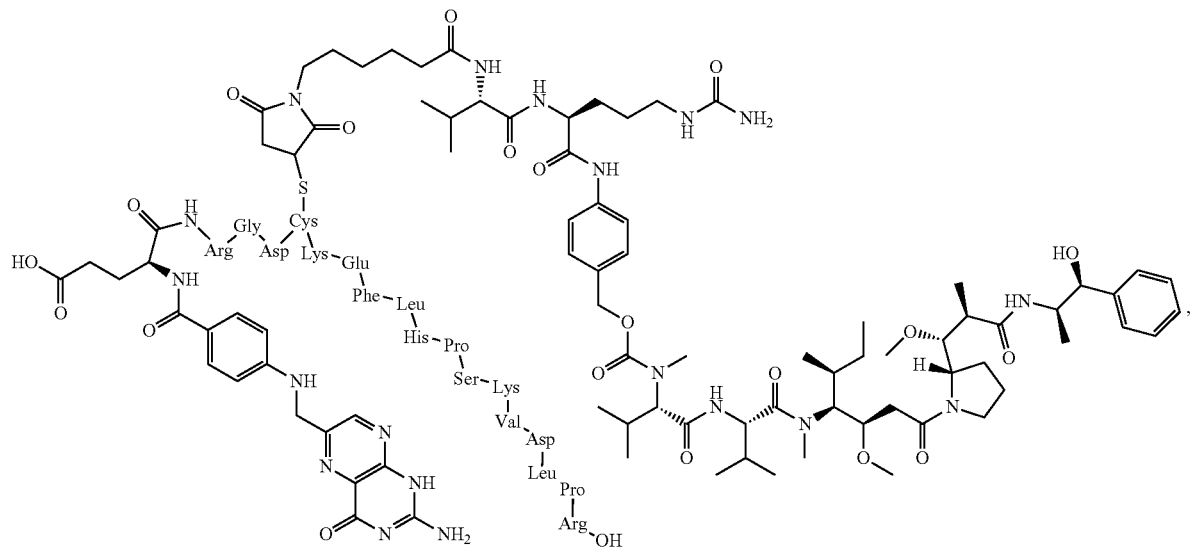
(LDC10BR)
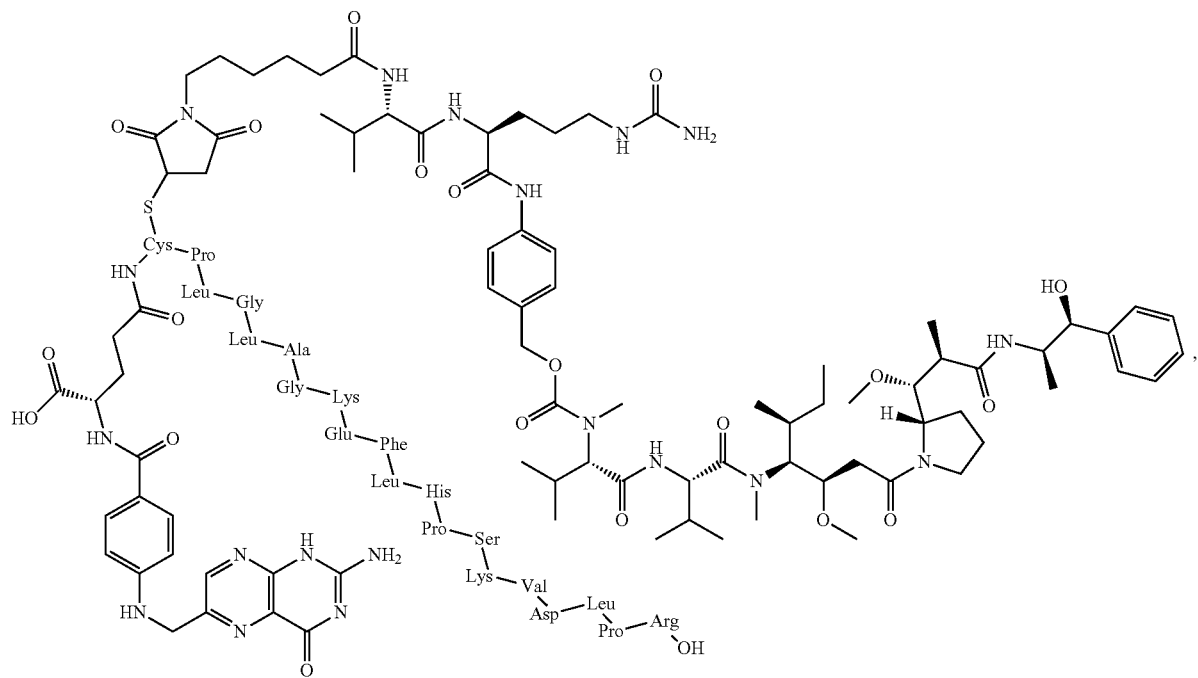
(LDC10BX)

(LDC11B)
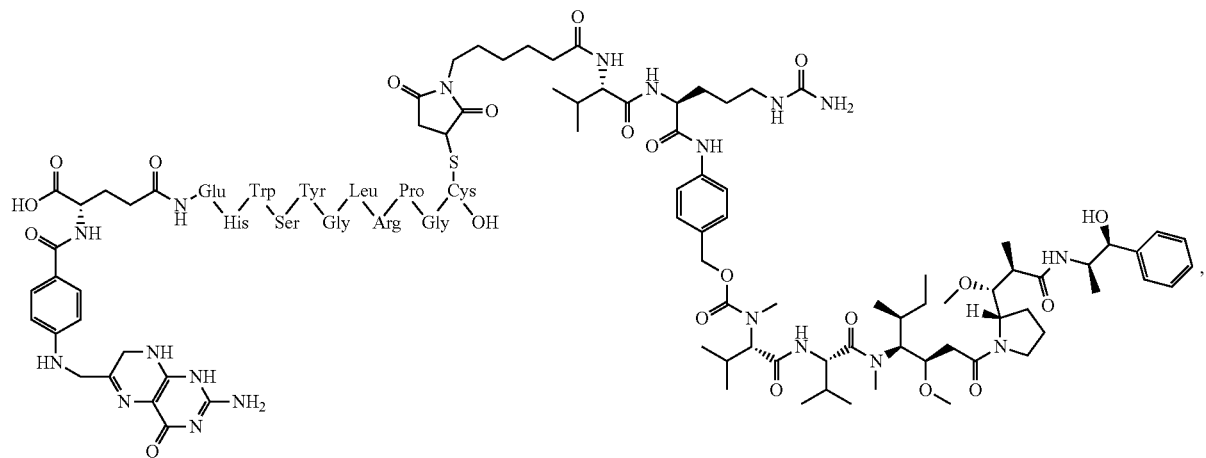
(LDC12B)
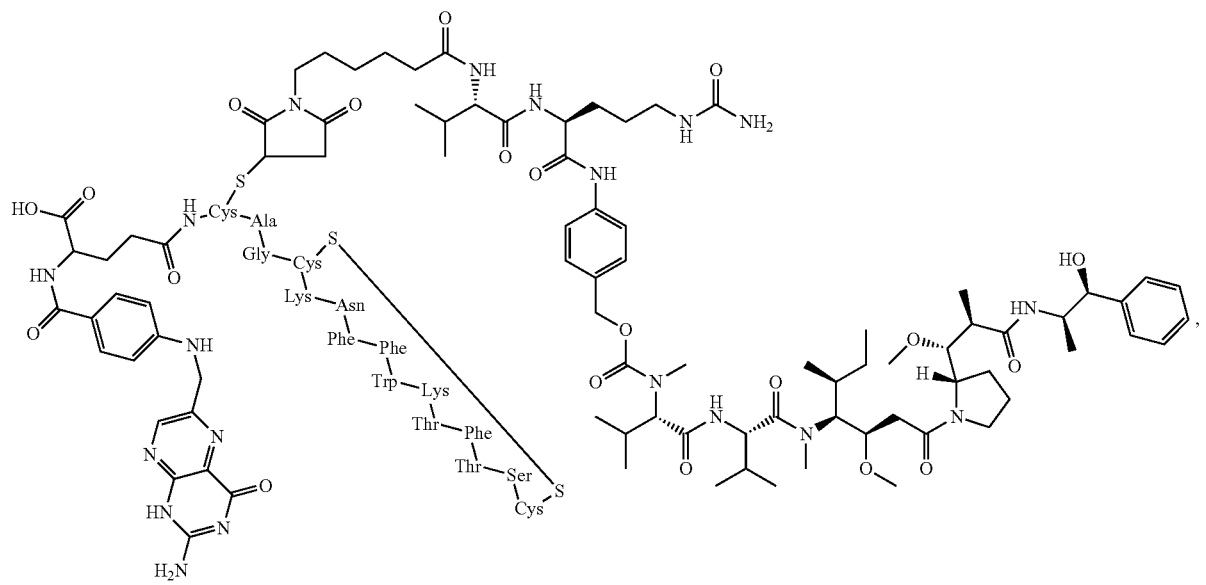
(LDC13B)
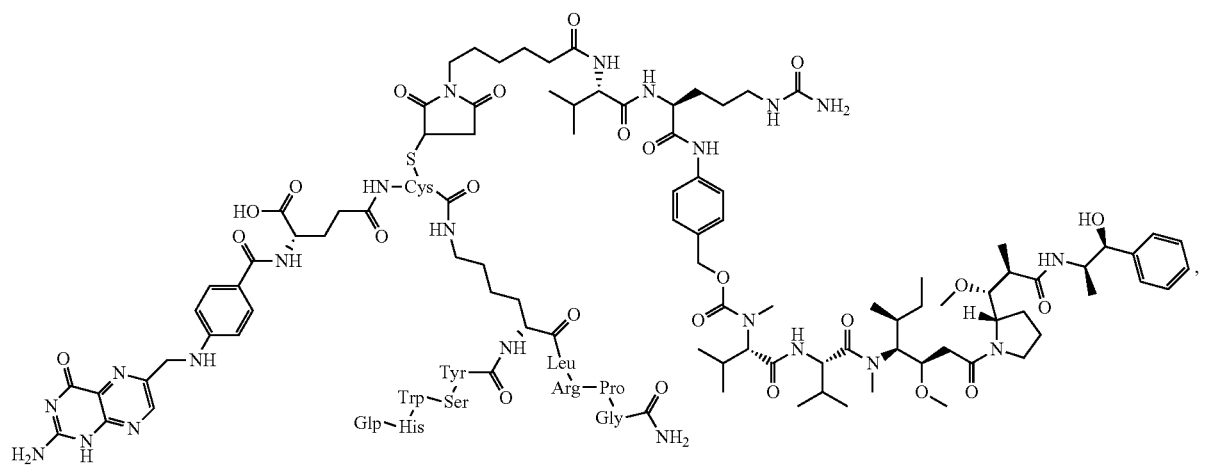

(LDC1013)
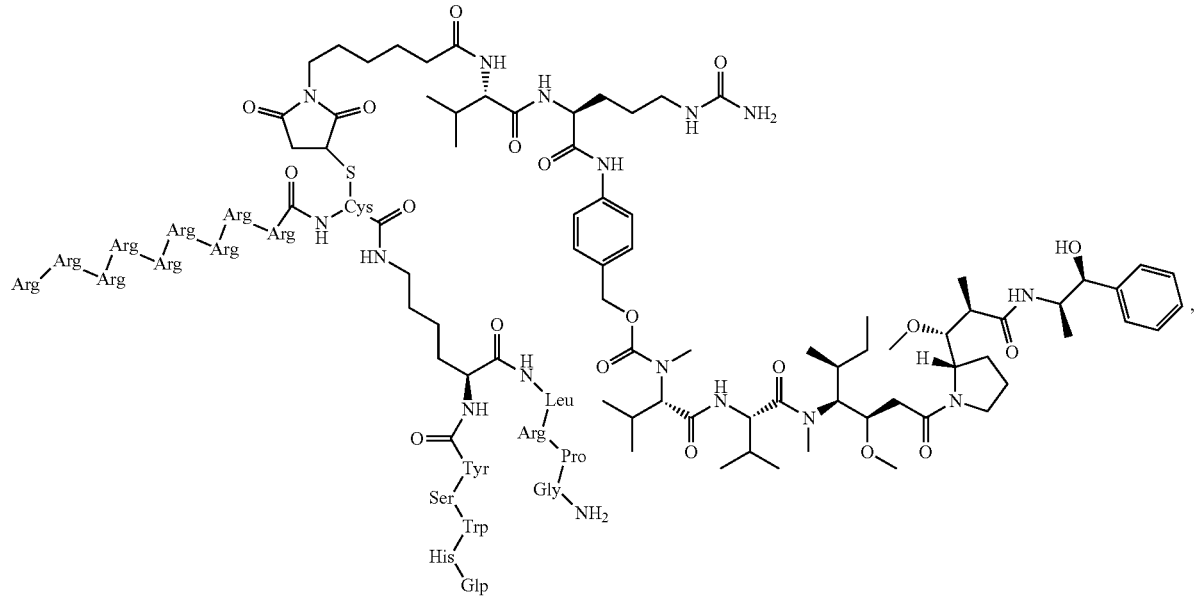
(LDC10H)
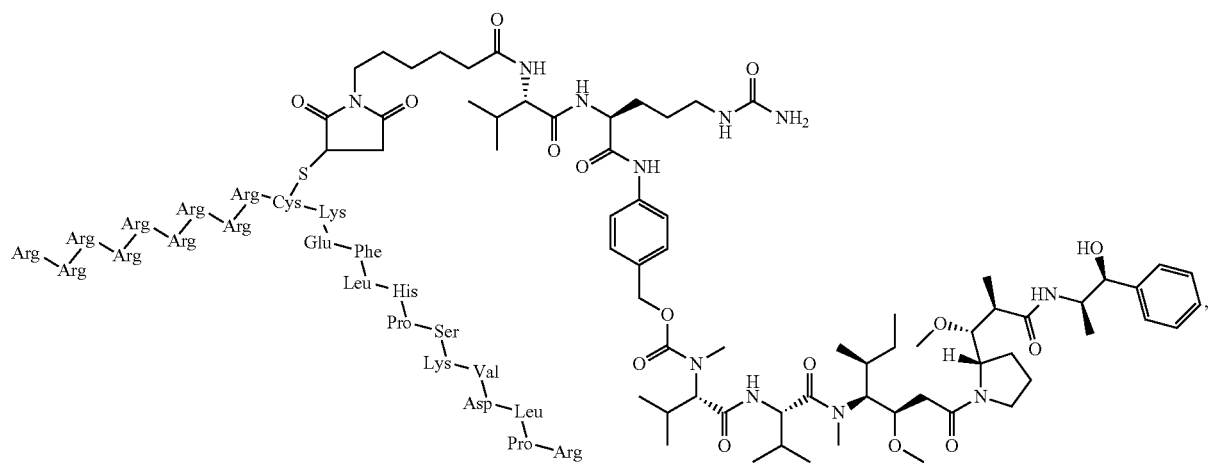
(LDC11H)
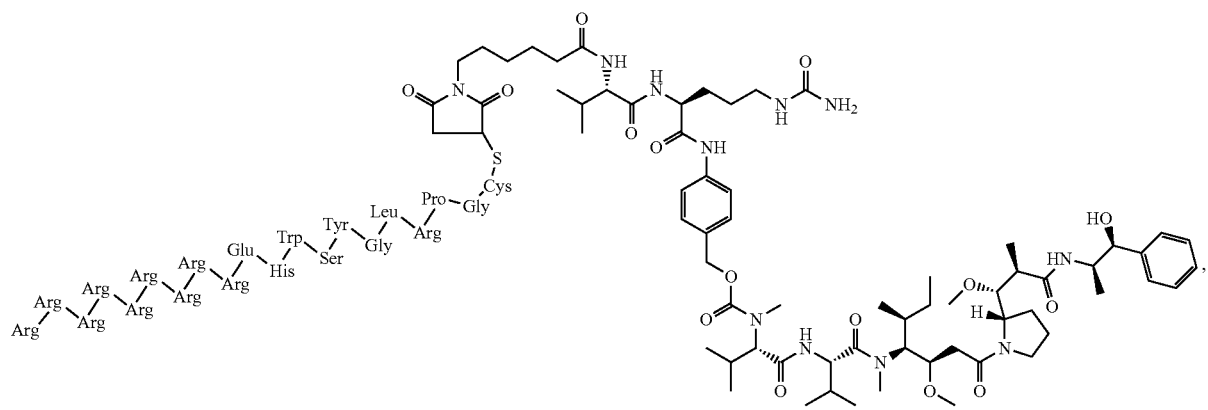

(LDC12H)

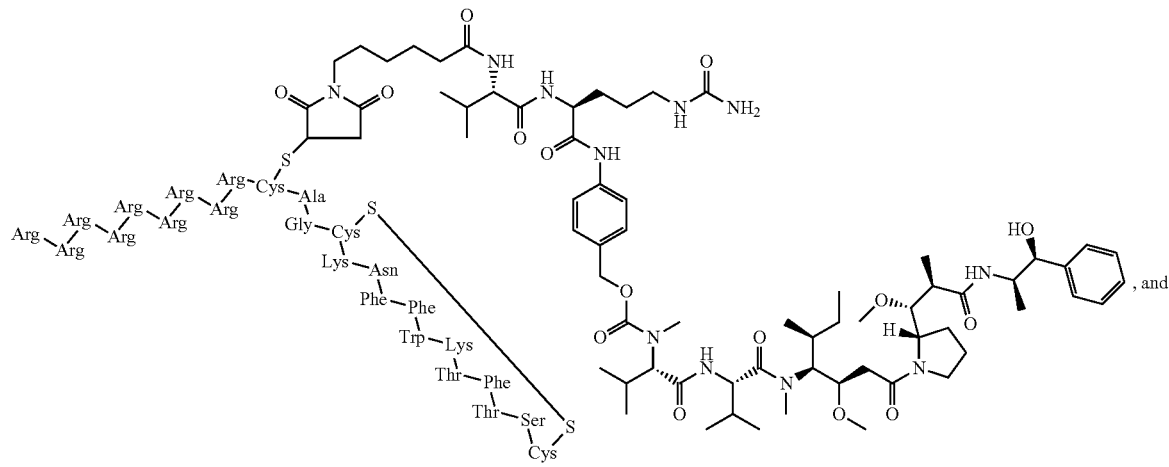

, and (LDC13H)

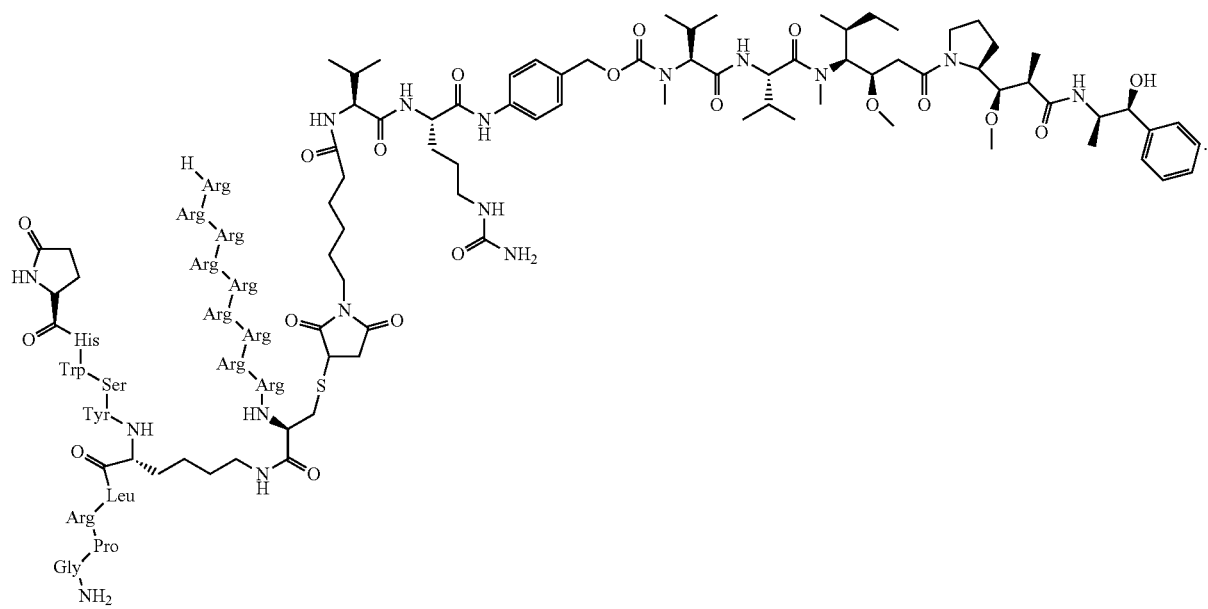

.

5. The conjugate compound of claim 1, or a pharmaceutically acceptable salt thereof, further comprising a third cell-interacting molecule, wherein the third cell-interacting molecule is the endocytosis molecule.

6. A pharmaceutical composition comprising the conjugate compound of claim 1, or a pharmaceutically acceptable salt thereof, and a pharmaceutically acceptable carrier.

* * * * *